(12) United States Patent
Miller et al.

(10) Patent No.: US 11,169,156 B2
(45) Date of Patent: **\*Nov. 9, 2021**

(54) LONG WAVELENGTH VOLTAGE SENSITIVE DYES

(71) Applicant: The Regents of the University of California, Oakland, CA (US)

(72) Inventors: Evan W. Miller, Kensington, CA (US); Yi-Lin Huang, Taipei (TW); Alison S. Walker, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 233 days.

This patent is subject to a terminal disclaimer.

(21) Appl. No.: 15/745,044

(22) PCT Filed: Jul. 28, 2016

(86) PCT No.: PCT/US2016/044577
§ 371 (c)(1),
(2) Date: Jan. 15, 2018

(87) PCT Pub. No.: WO2017/019908
PCT Pub. Date: Feb. 2, 2017

(65) Prior Publication Data
US 2018/0209987 A1 Jul. 26, 2018

Related U.S. Application Data

(60) Provisional application No. 62/197,905, filed on Jul. 28, 2015.

(51) Int. Cl.
*G01N 33/58* (2006.01)
*C07F 7/08* (2006.01)
(Continued)

(52) U.S. Cl.
CPC ........ *G01N 33/582* (2013.01); *C07F 7/0816* (2013.01); *C09B 69/008* (2013.01);
(Continued)

(58) Field of Classification Search
CPC ............. G01N 33/582; G01N 15/1475; G01N 33/48728; G01N 2015/1006; C07F 7/0816; C09B 69/008; C09B 69/06
(Continued)

(56) References Cited

U.S. PATENT DOCUMENTS 6,323,039 B1   11/2001  Dykens et al.
9,561,494 B2 *  2/2017  Kato ....................... F01N 3/103
(Continued)

FOREIGN PATENT DOCUMENTS

CN       104 262 378 A    1/2015
GB           749308       5/1956
(Continued)

OTHER PUBLICATIONS

Kushida et al. Silicon-substituted xanthene dyes and their applications in bioimaging, analyst, 2015, 140, 685-695.*
(Continued)

*Primary Examiner* — Ling Siu Choi
*Assistant Examiner* — Ronald Grinsted
(74) *Attorney, Agent, or Firm* — Gavrilovich, Dodd & Lindsey LLP

(57) ABSTRACT

The disclosure provides for provides for water-soluble near-infra red (NIR) emissive compounds, processes of making the compounds thereof, and use of the compounds therein.

7 Claims, 20 Drawing Sheets

(51) Int. Cl.
*C09B 69/00* (2006.01)
*C09B 69/06* (2006.01)
*G01N 15/14* (2006.01)
*G01N 33/48* (2006.01)
*G01N 33/487* (2006.01)
*G01N 15/10* (2006.01)

(52) U.S. Cl.
CPC ......... *C09B 69/06* (2013.01); *G01N 15/1475* (2013.01); *G01N 33/48728* (2013.01); *G01N 2015/1006* (2013.01)

(58) Field of Classification Search
USPC ........................................................ 252/589
See application file for complete search history.

(56) References Cited

U.S. PATENT DOCUMENTS

| 9,649,389 | B2 * | 5/2017 | Groves .............. A61K 49/0054 |
| 9,702,824 | B2 * | 7/2017 | Cong ................... G01N 31/221 |
| 2008/0095834 | A1 | 4/2008 | Weissig et al. |
| 2013/0252843 | A1 | 9/2013 | Yan et al. |
| 2014/0314677 | A1 | 10/2014 | Groves et al. |
| 2015/0330892 | A1 | 11/2015 | Cerignoli et al. |

FOREIGN PATENT DOCUMENTS

| WO | 2012/159116 A2 | 11/2012 |
| WO | 2013/029650 A1 | 3/2013 |
| WO | WO2013/029650 | * 3/2013 |
| WO | 2014/144793 A1 | 9/2014 |
| WO | 2015/175870 A1 | 11/2015 |
| WO | 2016054412 A1 | 4/2016 |

OTHER PUBLICATIONS

Cervigni, S., Extended European Search Report, Application No. 16831378.1, European Patent Office, dated Feb. 28, 2019.
Kushida Yu et al, "Silicon-substituted xanthene dyes and their applications in bioimaging", The Analyst, vol. 140, No. 3, Oct. 14, 2014, pp. 685-695.
Copenheaver, Blaine R., International Search Report and Written Opinion, PCT/US2016/044577, United States Patent and Trademark Office, dated Dec. 9, 2016.
Nickitas-Etienne, Athina., International Preliminary Report on Patentability and Written Opinion, PCT/US2016/044577, The International Bureau of WIPO, dated Feb. 8, 2018.
Cervigni, S., Partial European Search Report, European Patent Office, Application No. 16831378.1, dated Nov. 20, 2018.
Chevalier, Arnaud et al., "Rapid Synthesis of Unsymmetrical Sulforhodamines Through Nucleophilic Amination of a Monobrominated Sulfoxanthene Dye: Rapid Synthesis of Unsymmetrical Sulforhodamines", European Journal of Organic Chemistry, vol. 2015, No. 1, Nov. 5, 2014, pp. 152-165.
Li, Yao, Office Action, Chinese Patent Office, Application No. 2016800545481, dated Mar. 2, 2020.

* cited by examiner

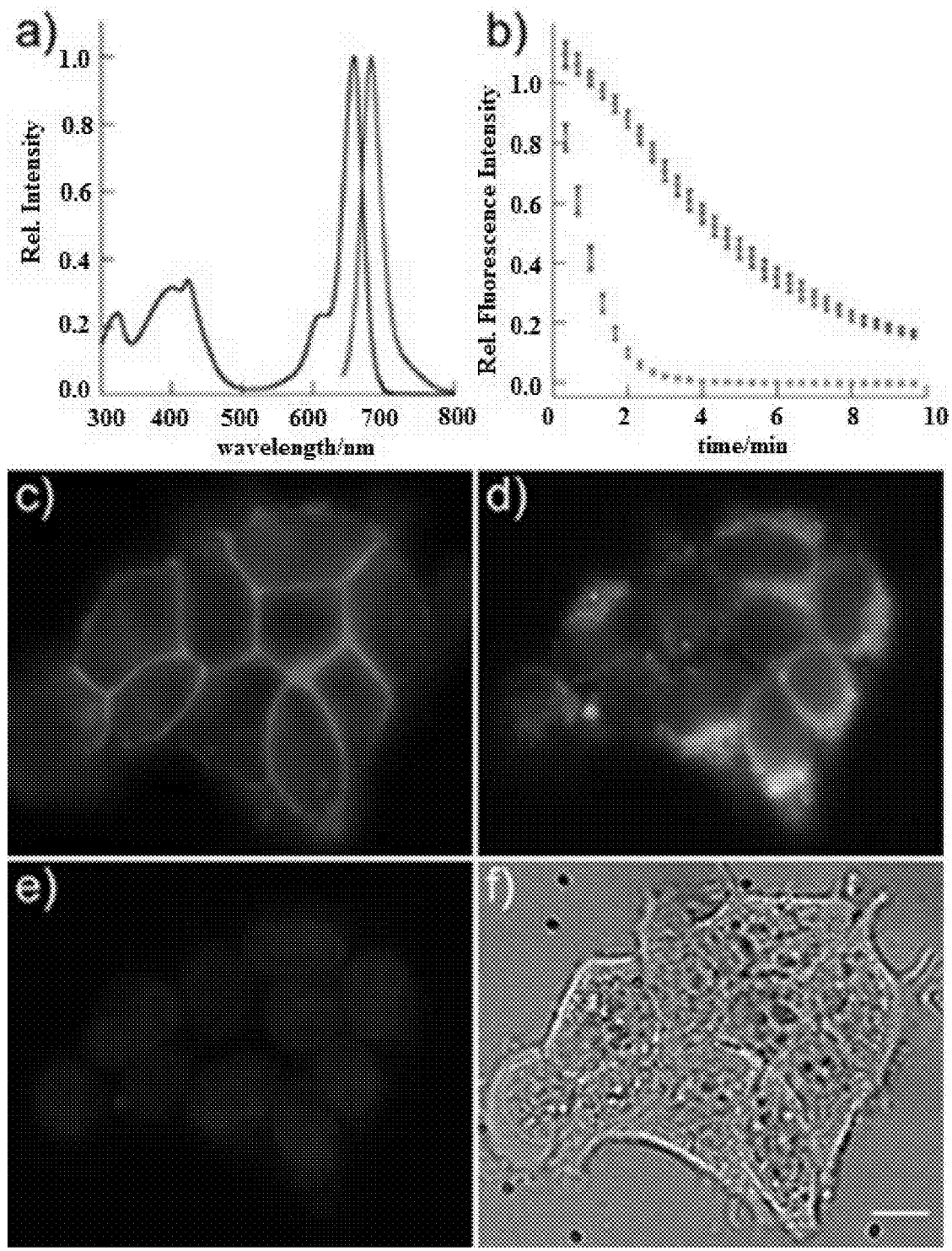
*FIG. 1A-F*

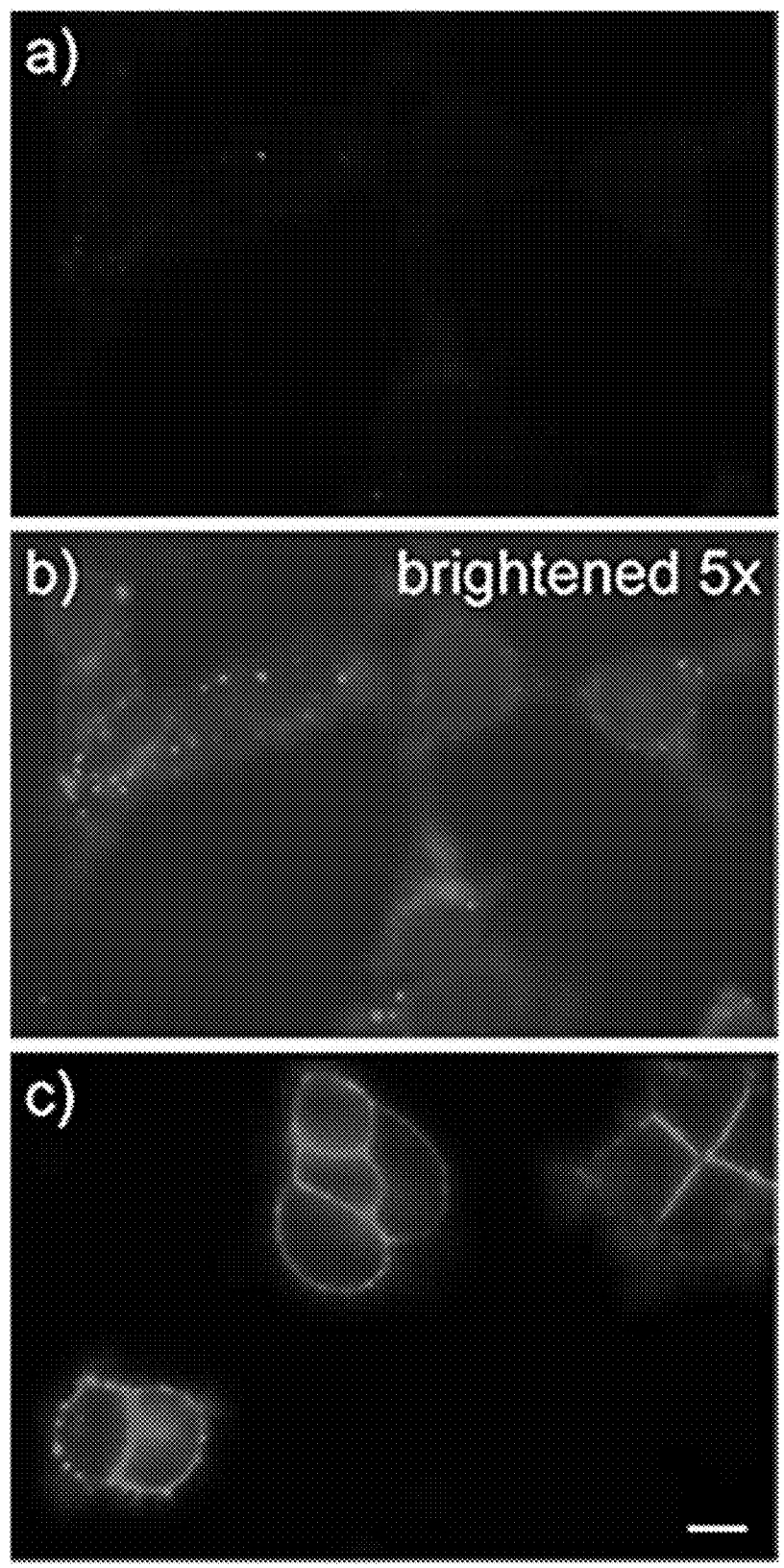
FIG. 3A-C

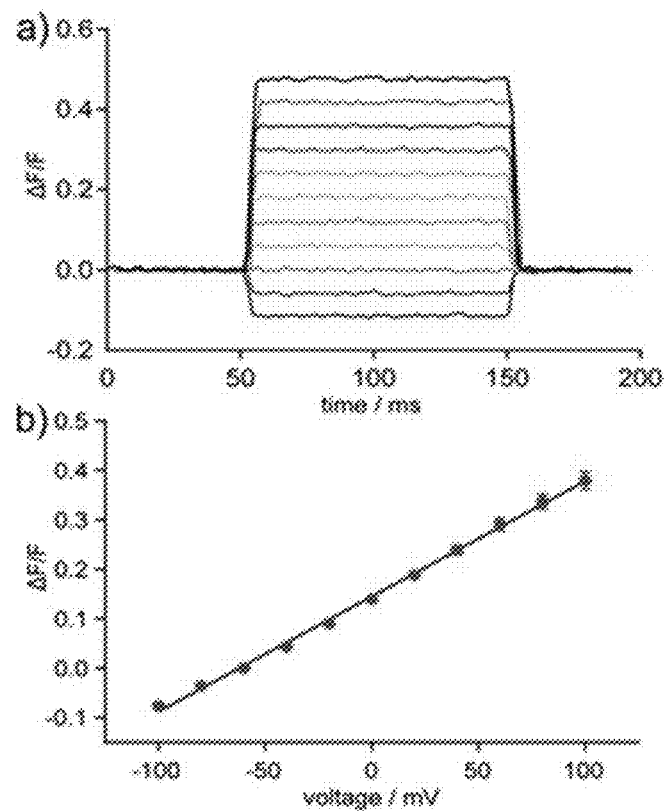
FIG. 4A-B
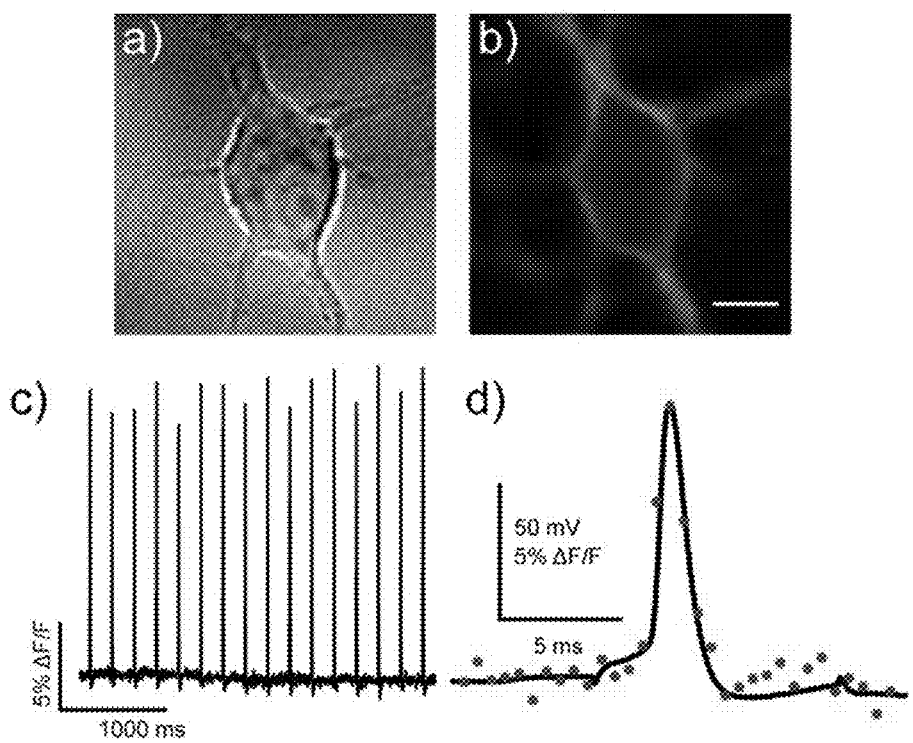
FIG. 5A-D

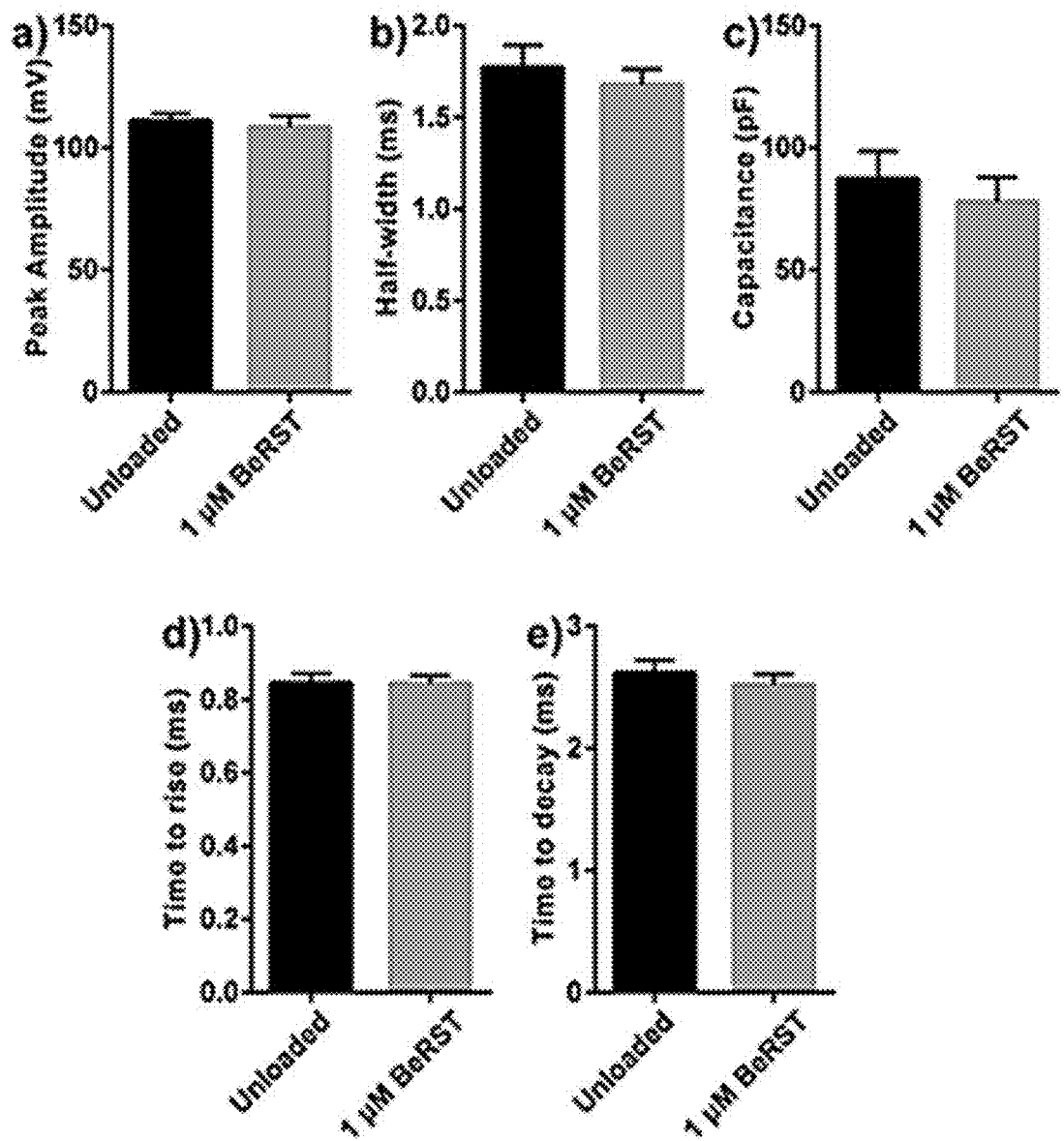
FIG. 6A-E

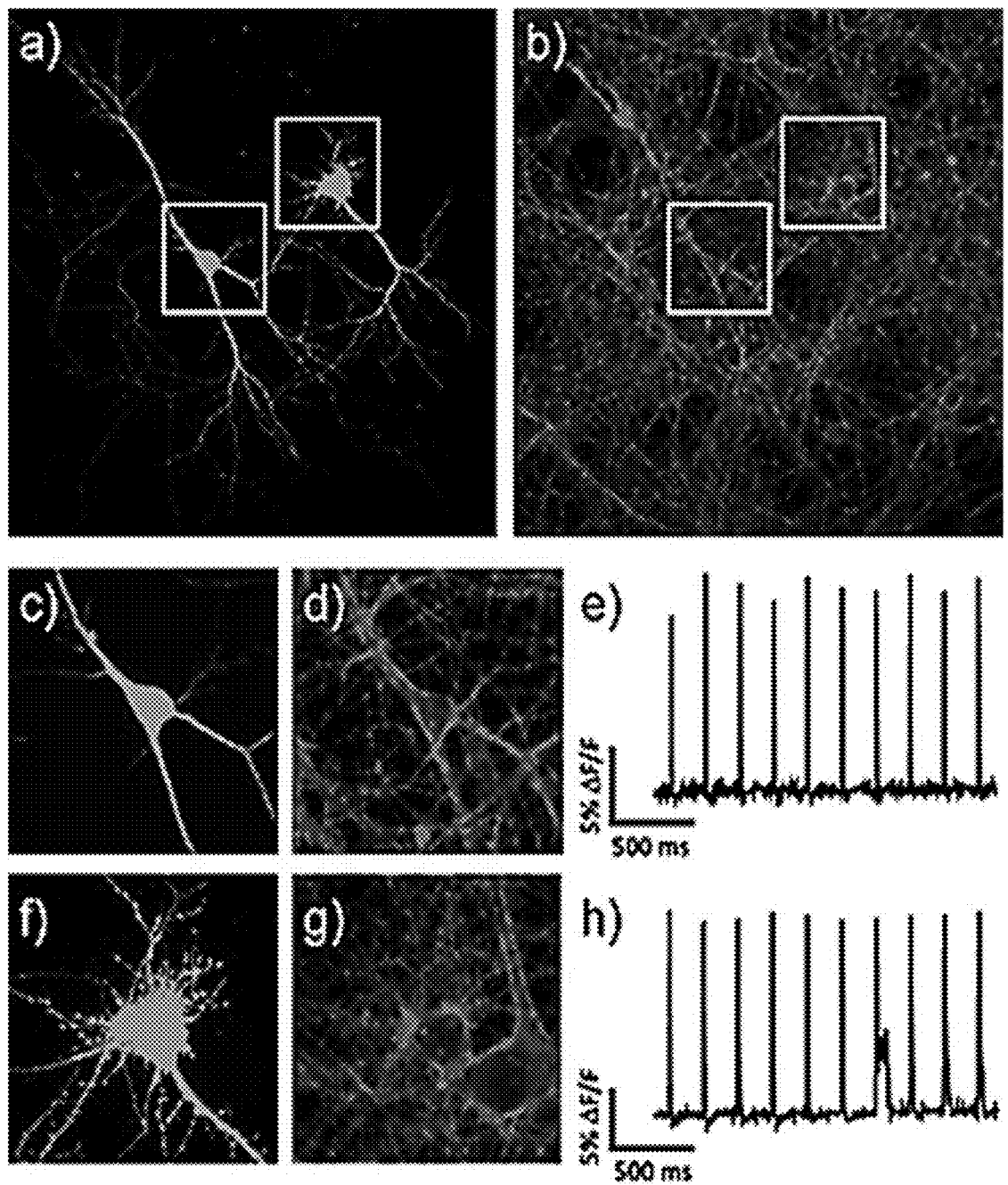
FIG. 7A-H

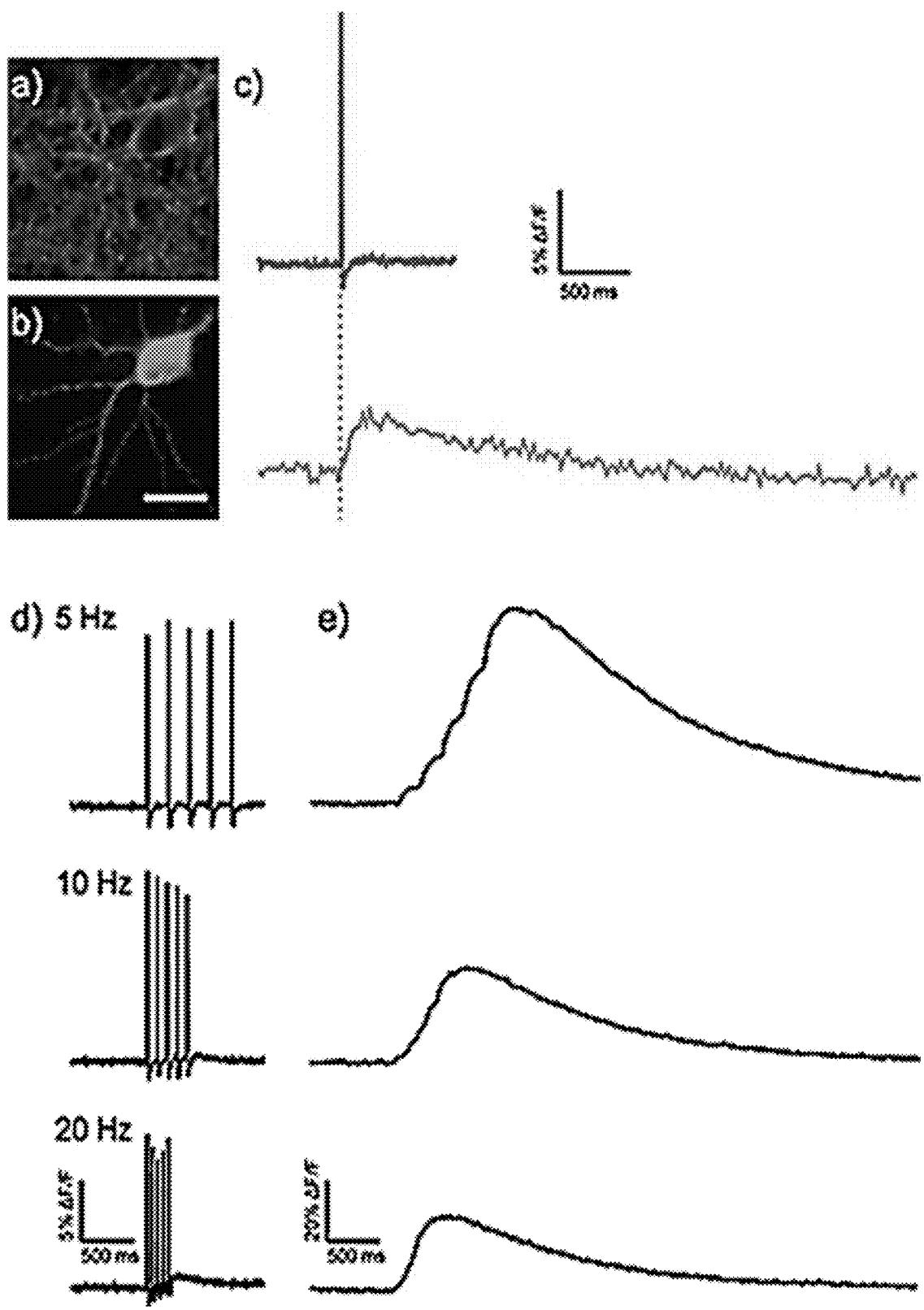
FIG. 9A-E

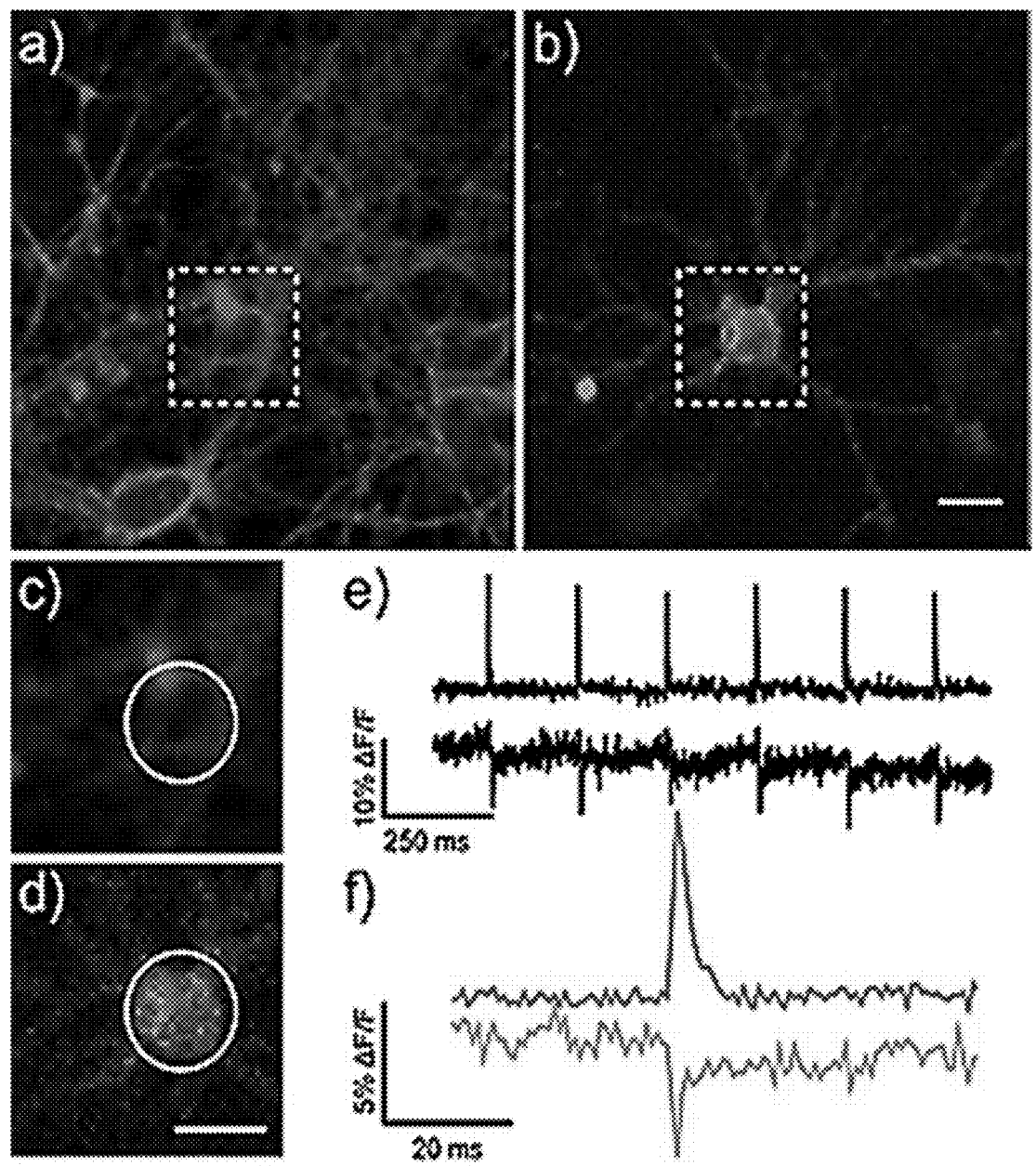
FIG. 10A-F

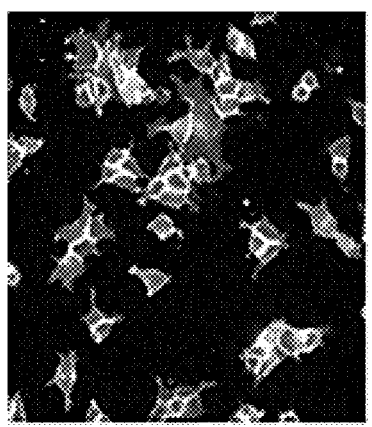  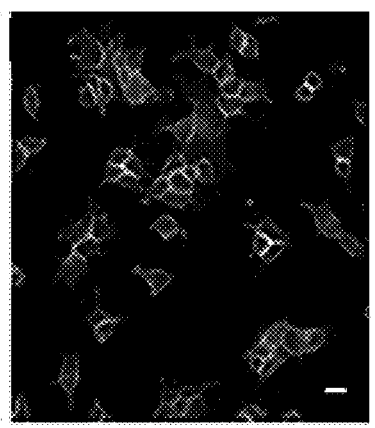
FIG. 11A  FIG. 11B  FIG. 11C
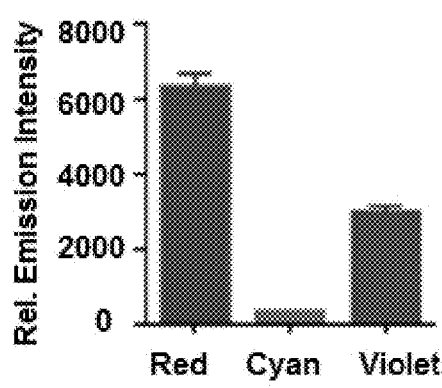 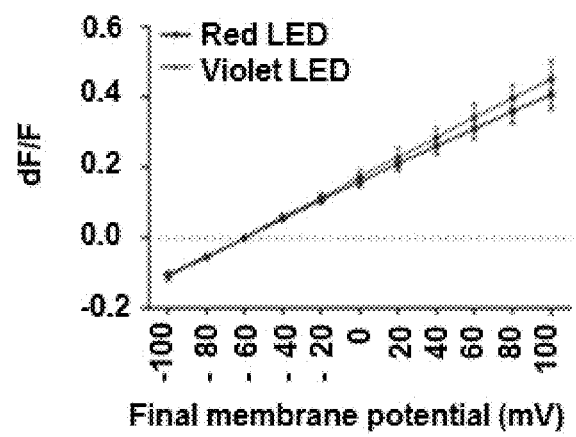
FIG. 11D  FIG. 11E

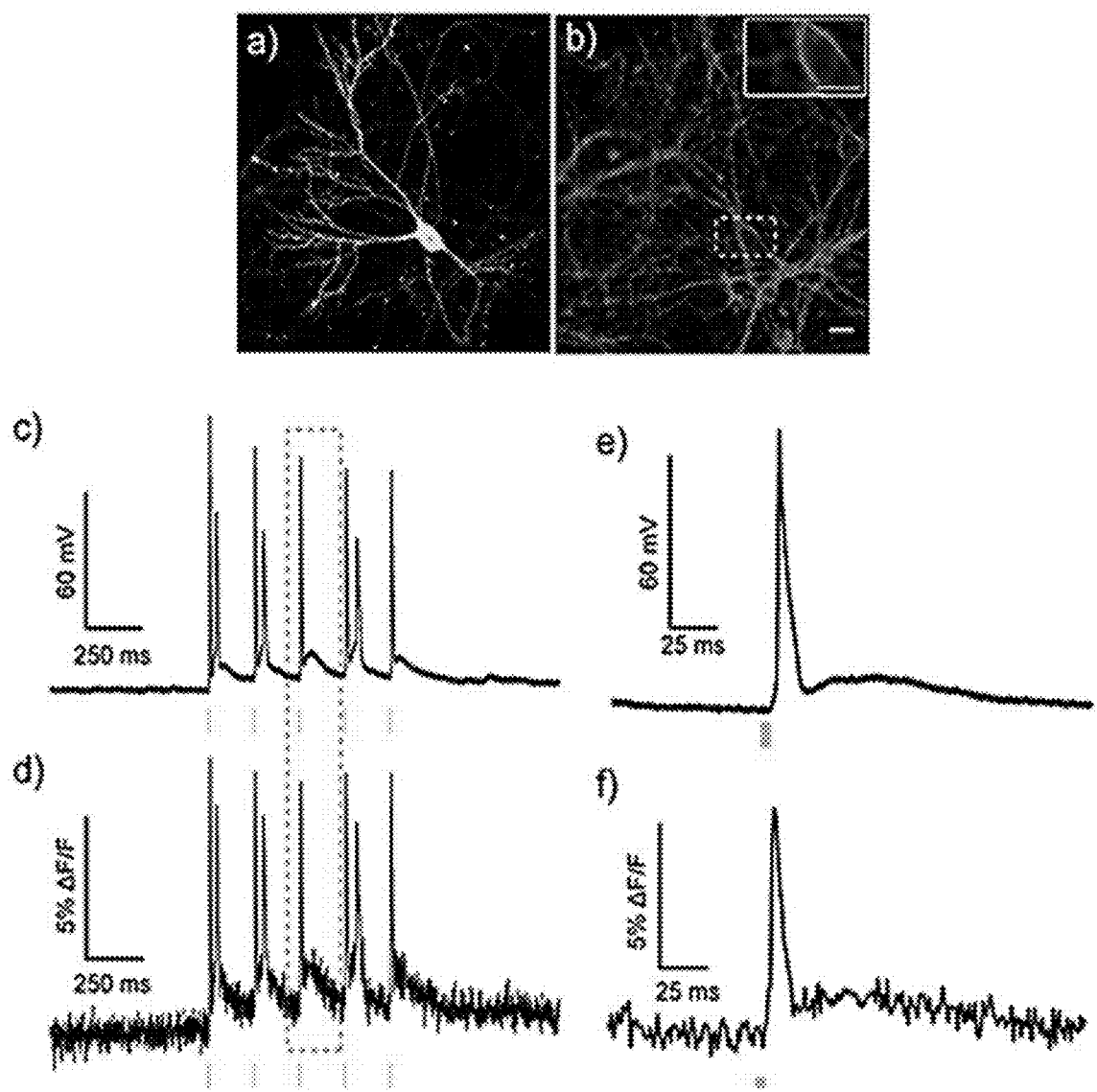
FIG. 13A-F

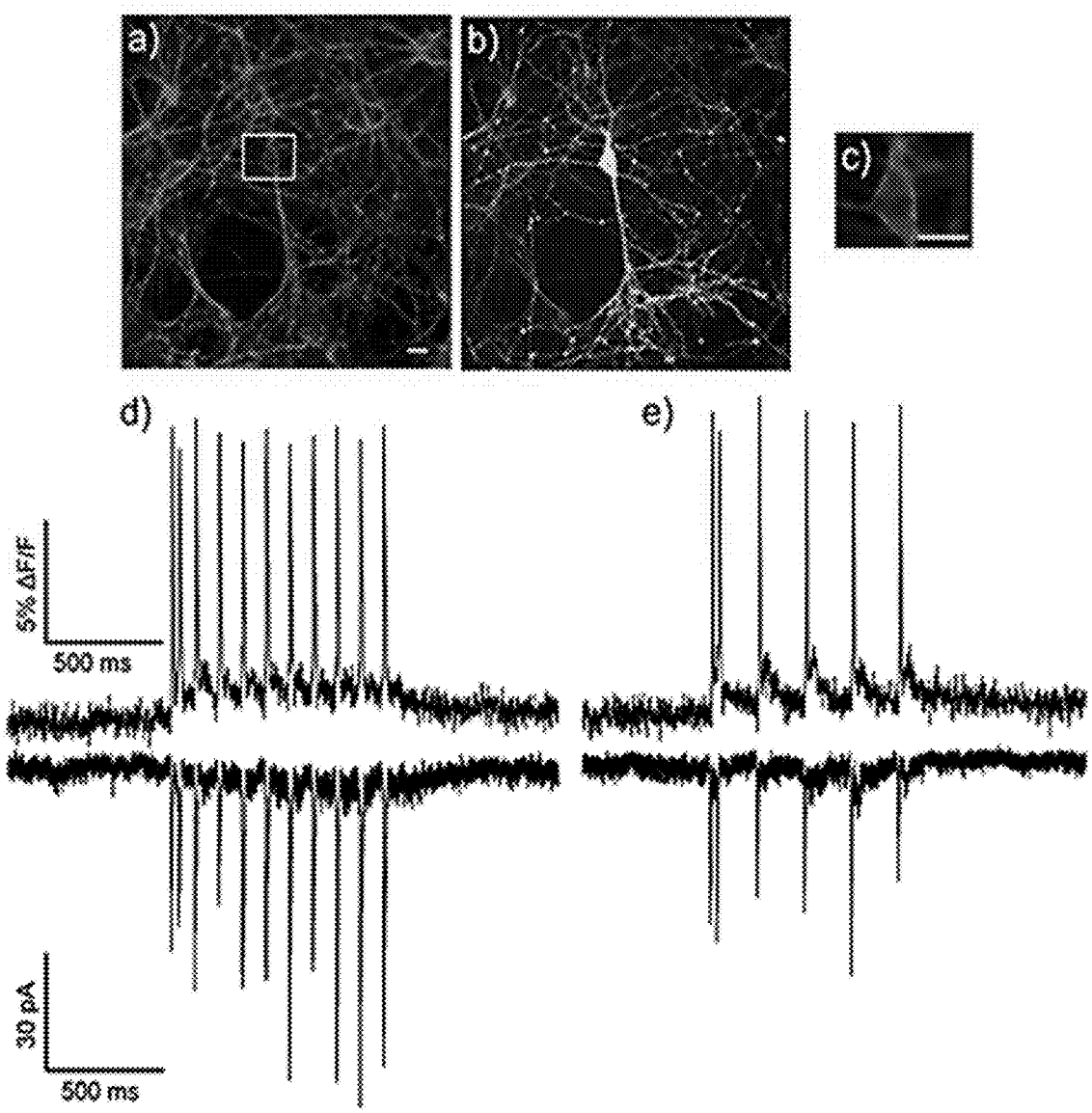
FIG. 14A-E

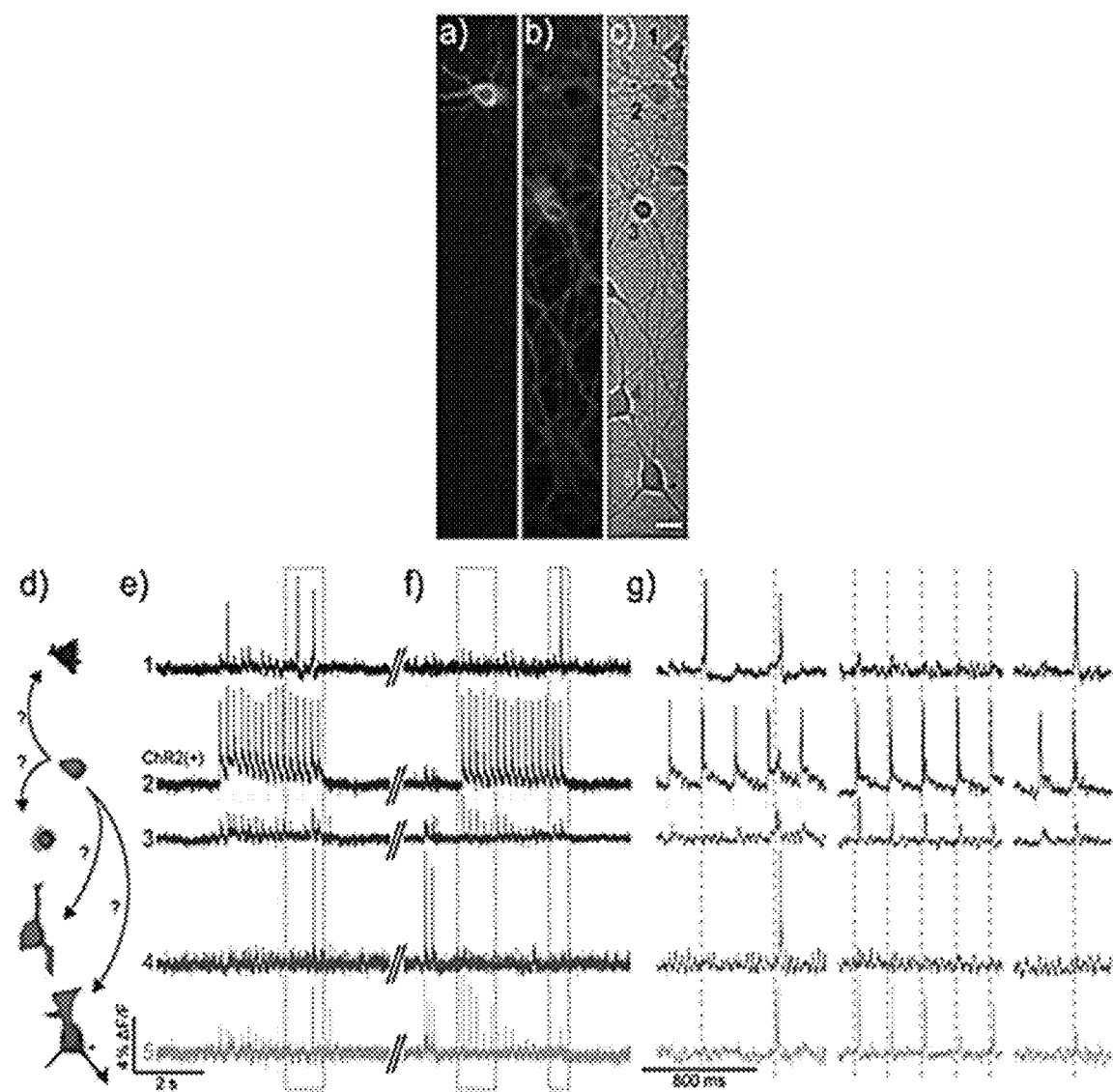
FIG. 15A-G

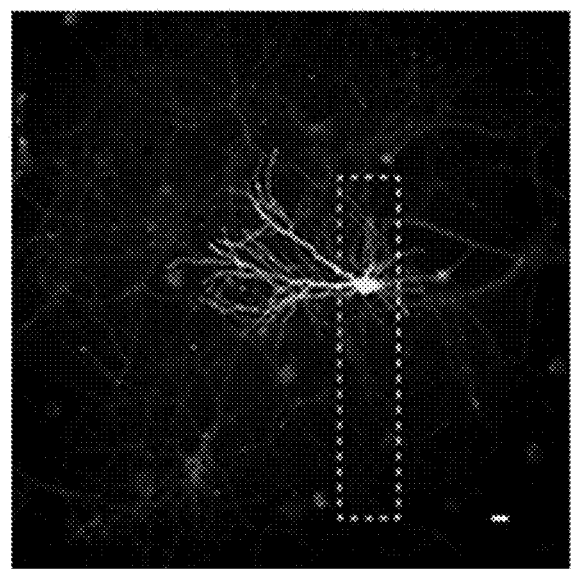
FIG. 16
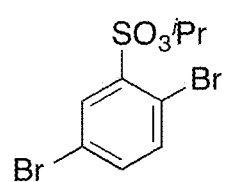
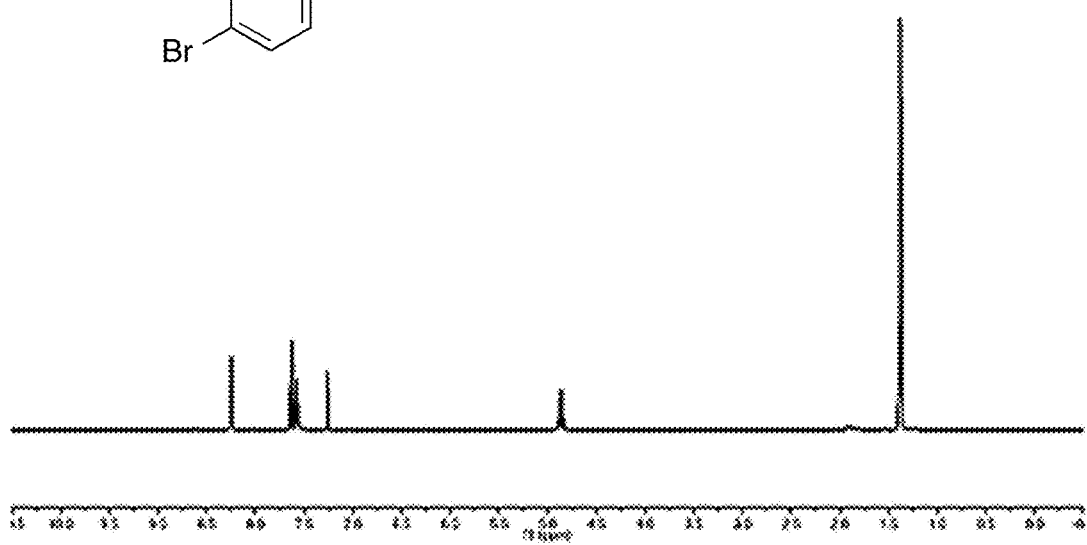
FIG. 17

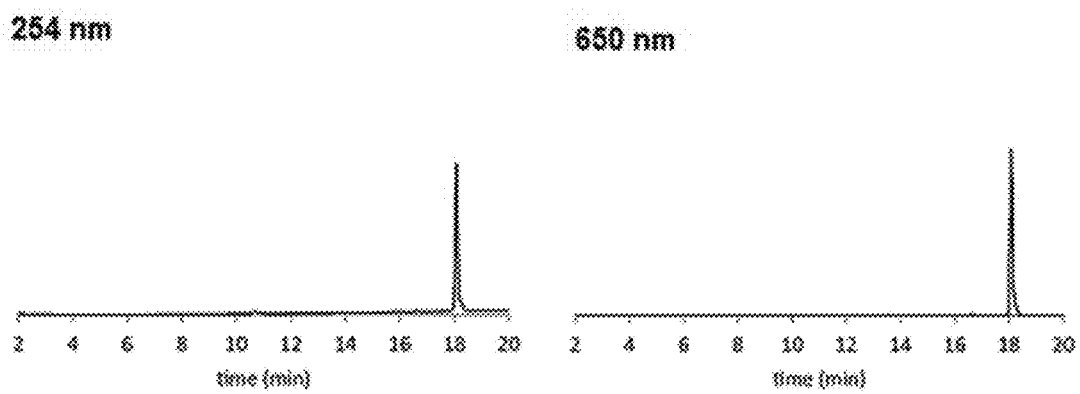
FIGURE 25
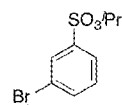
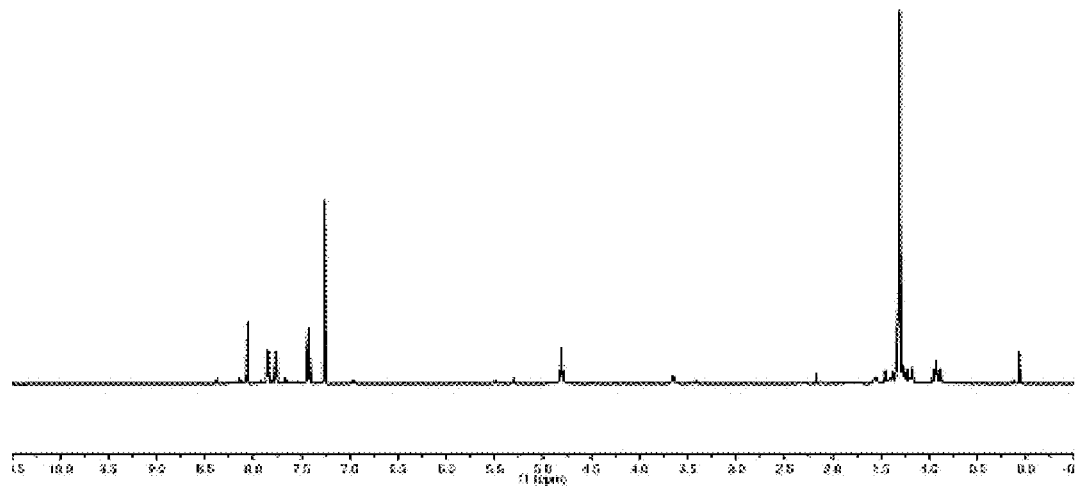
FIGURE 26

LONG WAVELENGTH VOLTAGE SENSITIVE DYES

CROSS REFERENCE TO RELATED APPLICATIONS

This application is a U.S. National Stage Application filed under 35 U.S.C. § 371 and claims priority to International Application No. PCT/US2016/044577, filed Jul. 28, 2016, which claims priority under 35 U.S.C. § 119 from Provisional Application Ser. No. 62/197,905, filed Jul. 28, 2015, the disclosures of which are incorporated herein by reference.

GOVERNMENT LICENSE RIGHTS

This invention was made with Government support under Grant No. NS078561, awarded by National Institutes of Health. The Government has certain rights in the invention.

TECHNICAL FIELD

The disclosure provides for water-soluble far red to near-infra red (NIR) emissive compounds, processes of making the compounds thereof, and use of the compounds therein.

BACKGROUND

Rapid changes in the membrane potential ($V_{mem}$) of excitable cells like neurons and cardiomyocytes play a central role in defining cellular signaling and physiological profiles of these specialized cells. Classically, $V_{mem}$ is monitored and measured via patch clamp electrophysiology, in which a microelectrode attached to the cell of interest enables highly sensitive recordings of membrane voltage with exquisite temporal resolution. The use of electrodes, however, is highly invasive, limits records to the soma of a single cell (space clamp error), and is extremely low throughput.

SUMMARY

The disclosure provides the design and synthesis of a photostable, near-infra red (NIR) platform for optical voltage sensing. The compounds of the disclosure are a class of NIR voltage sensitive dyes that make use of a photoinduced electron transfer (PeT) trigger for optical interrogation of membrane voltage. The compounds disclosed herein display bright, membrane-localized NIR fluorescence in living cells, have high photostability, and shows excellent voltage sensitivity in neurons. The compounds of the disclosure can be used with fluorescent stains for organelles, $Ca^{2+}$ indicators, and voltage-sensitive fluorescent proteins; and can be used in conjunction with optogenetic actuators. The high speed, sensitivity, photostability and NIR fluorescence profiles of compounds of the disclosure make the compounds a useful platform for studying neuronal activity non-invasively.

The disclosure provides a compound comprising the structure of Formula I:

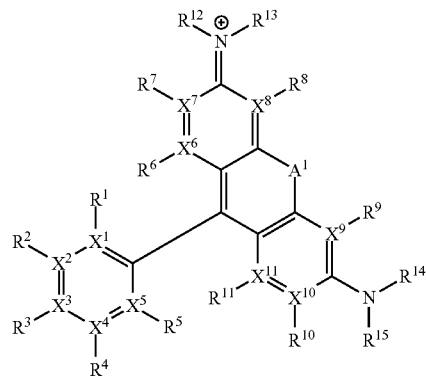

Formula I wherein $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of H, D, optionally substituted FG, optionally substituted ($C_1$-$C_{12}$)alkyl, optionally substituted ($C_1$-$C_{11}$)heteroalkyl, optionally substituted ($C_1$-$C_{12}$) alkenyl, optionally substituted ($C_1$-$C_{11}$)heteroalkenyl, optionally substituted ($C_1$-$C_{12}$)alkynyl, and optionally substituted ($C_1$-$C_{11}$)heteroalkynyl; $X^1$-$X^{11}$ are independently selected from N or C, wherein when an X group is an N, then the R group is absent; and $R^1$-$R^{15}$ are independently selected from H, D, optionally substituted FG, optionally substituted ($C_1$-$C_{12}$)alkyl, optionally substituted ($C_1$-$C_{11}$)heteroalkyl, optionally substituted ($C_1$-$C_{12}$) alkenyl, optionally substituted ($C_1$-$C_{11}$)heteroalkenyl, optionally substituted ($C_1$-$C_{12}$) alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system, and wherein at least one of $R^1$ to $R^5$ is a sulfonate group.

In a further embodiment, the disclosure also provides for a compound which comprises the structure of Formula I(a):

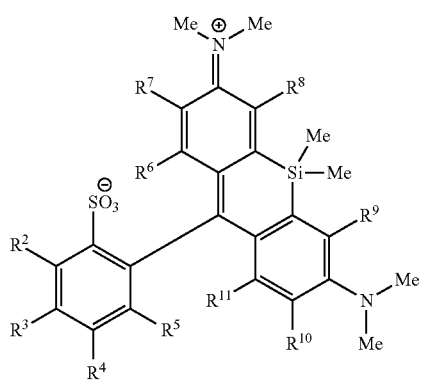

Formula I(a)

wherein, $R^2$-$R^{11}$ are independently selected from H, D, optionally substituted FG, optionally substituted ($C_1$-$C_6$) alkyl, optionally substituted ($C_1$-$C_5$)heteroalkyl, optionally substituted ($C_1$-$C_6$)alkenyl, optionally substituted ($C_1$-$C_5$) heteroalkenyl, optionally substituted ($C_1$-$C_6$)alkynyl, optionally substituted (C₁-C₅)heteroalkynyl, optionally substituted (C₅-C₇)cycloalkyl, optionally substituted (C₅-C₇)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In a yet another embodiment, the disclosure provides for a compound that comprises the structure of:

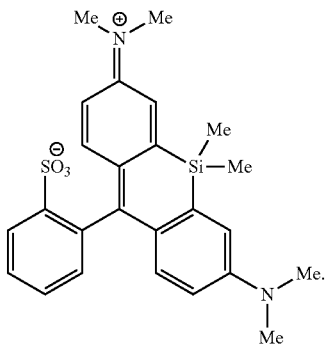

In another embodiment, the disclosure provides for a compound that comprises the structure of:

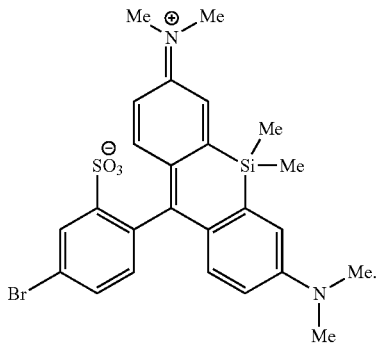

The disclosure also provides for a compound which comprises the structure of Formula II:

Formula II

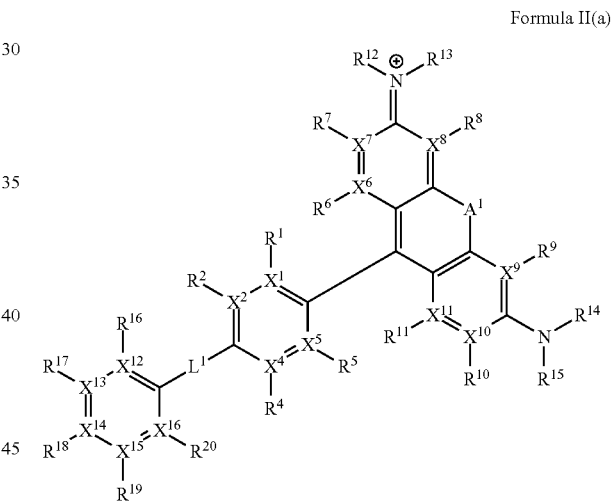

wherein, A¹ is selected from CH₂, CHR', CR'₂, NH, O, S, Se, Te, SiH₂, SiHR', SiR'₂, GeH₂, GeHR', GeR'₂, SnH₂, SnHR', SnR'₂, PbH₂, PbHR', or PbHR'₂, wherein R' is selected from the group consisting of H, D, optionally substituted FG, optionally substituted (C₁-C₁₂)alkyl, optionally substituted (C₁-C₁₁)heteroalkyl, optionally substituted (C₁-C₁₂)alkenyl, optionally substituted (C₁-C₁₁)heteroalkenyl, optionally substituted (C₁-C₁₂)alkynyl, and optionally substituted (C₁-C₁₁)heteroalkynyl; W¹ is a molecular wire moiety; X¹, X², and X⁴-X¹¹ are independently selected from N or C, wherein when an X group is an N, then the R group is absent; R¹, R², and R⁴-R¹⁵ are independently selected from H, D, optionally substituted FG, optionally substituted (C₁-C₁₂)alkyl, optionally substituted (C₁-C₁₁)heteroalkyl, optionally substituted (C₁-C₁₂)alkenyl, optionally substituted (C₁-C₁₁)heteroalkenyl, optionally substituted (C₁-C₁₂)alkynyl, optionally substituted (C₁-C₁₁)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

The disclosure also provides for a compound comprising the structure of Formula II(a):

Formula II(a)

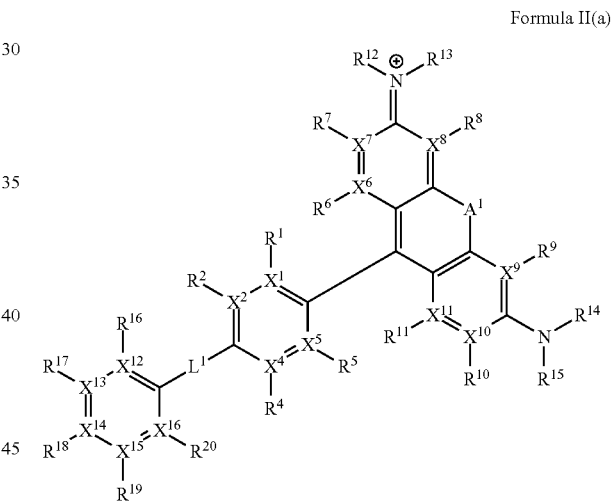

wherein, L¹ is selected from the group consisting of:

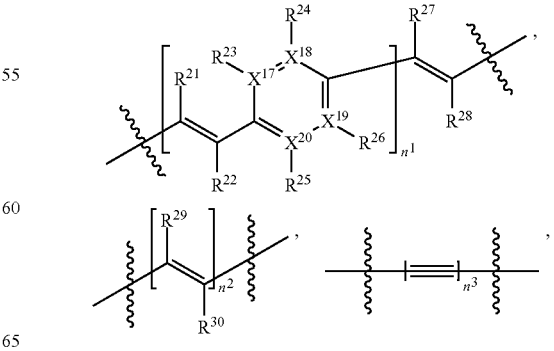

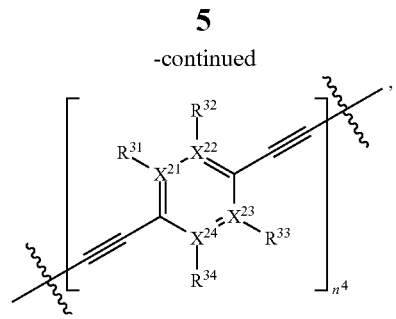

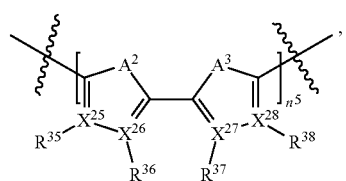

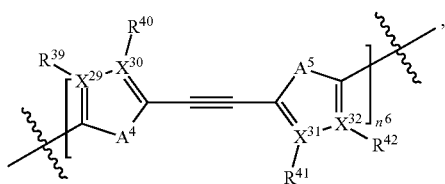

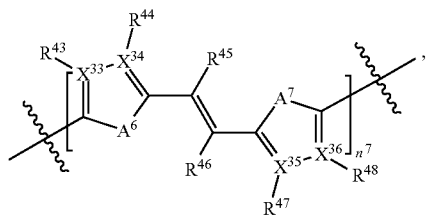

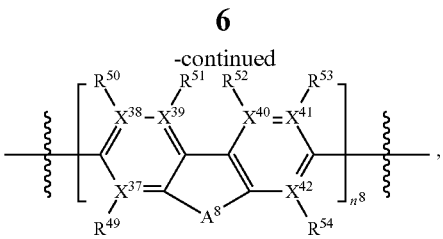

and any combination of the foregoing; $A^1$-$A^8$ are each independently selected from $CH_2$, CHR', CR'$_2$, NH, O, S, Se, Te, $SiH_2$, SiHR', SiR'$_2$, $GeH_2$, GeHR', GeR'$_2$, $SnH_2$, SnHR', SnR'$_2$, $PbH_2$, PbHR', or PbHR'$_2$, wherein R' is selected from the group consisting of H, D, optionally substituted FG, optionally substituted ($C_1$-$C_{12}$)alkyl, optionally substituted ($C_1$-$C_{11}$)heteroalkyl, optionally substituted ($C_1$-$C_{12}$) alkenyl, optionally substituted ($C_1$-$C_{11}$) heteroalkenyl, optionally substituted ($C_1$-$C_{12}$)alkynyl, and optionally substituted ($C_1$-$C_{11}$)heteroalkynyl; $X^1$, $X^2$, and $X^4$-$X^{42}$ are independently selected from N or C, wherein when an X group is an N, then the R group is absent; $R^1$, $R^2$, and $R^4$-$R^{54}$ are independently selected from H, D, optionally substituted FG, optionally substituted ($C_1$-$C_{12}$)alkyl, optionally substituted ($C_1$-$C_{11}$)heteroalkyl, optionally substituted ($C_1$-$C_{12}$) alkenyl, optionally substituted ($C_1$-$C_{11}$)heteroalkenyl, optionally substituted ($C_1$-$C_{12}$)alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $n^1$-$n^8$ are independently an integer selected from 0 to 10.

In a particular embodiment, the disclosure further provides for a compound comprising Formula II(b):

Formula II(b)

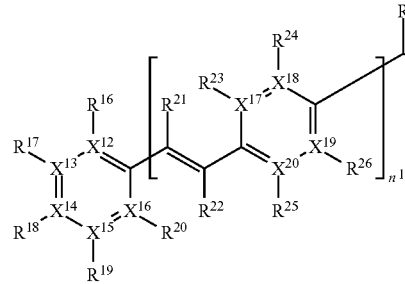

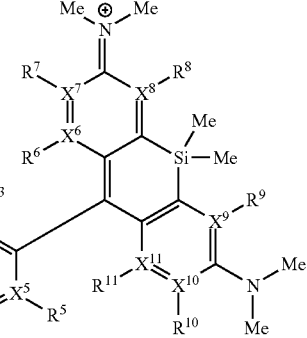

wherein, $X^1$, $X^2$, and $X^4$-$X^{20}$ are independently selected from N or C, wherein when an X group is an N, then the R group is absent; $R^2$, $R^4$-$R^{11}$, and $R^{16}$-$R^{26}$ are independently selected from H, D, optionally substituted FG, optionally substituted ($C_1$- $C_6$)alkyl, optionally substituted ($C_1$-$C_5$) heteroalkyl, optionally substituted ($C_1$-$C_6$)alkenyl, optionally substituted ($C_1$-$C_5$)heteroalkenyl, optionally substituted ($C_1$-$C_6$)alkynyl, optionally substituted ($C_1$- $C_5$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $n^1$ is an integer from 0 to 5.

In a certain embodiment, the disclosure provides for a compound which comprises the structure of Formula II(c):

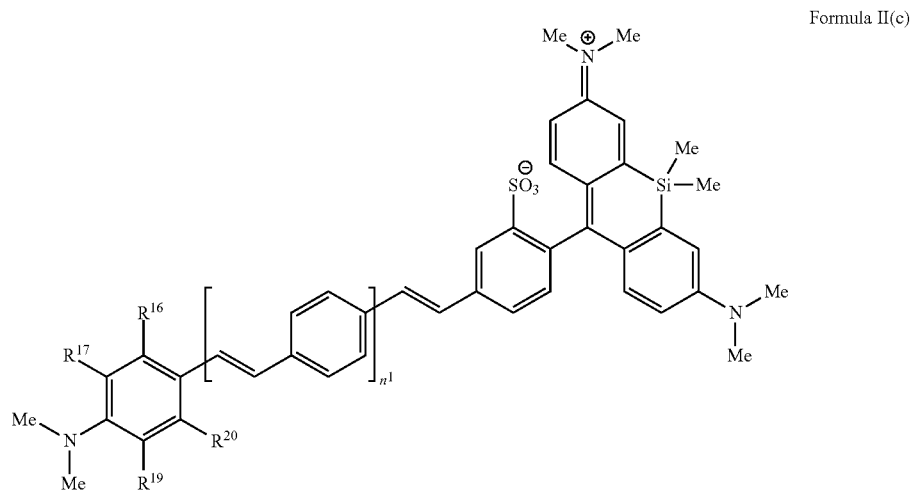

Formula II(c)

wherein, $R^{16}$, $R^{17}$, $R^{19}$ and $R^{20}$ are independently selected from H, D, optionally substituted FG, optionally substituted ($C_1$- $C_6$)alkyl, optionally substituted ($C_1$-$C_5$)heteroalkyl, optionally substituted ($C_1$-$C_6$) alkenyl, optionally substituted ($C_1$-$C_5$) heteroalkenyl, optionally substituted ($C_1$-$C_6$)alkynyl, optionally substituted ($C_1$- $C_5$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; $n^1$ is an integer from 0 to 5.

In yet a further embodiment, the disclosure also provides for a compound that comprises the structure of:

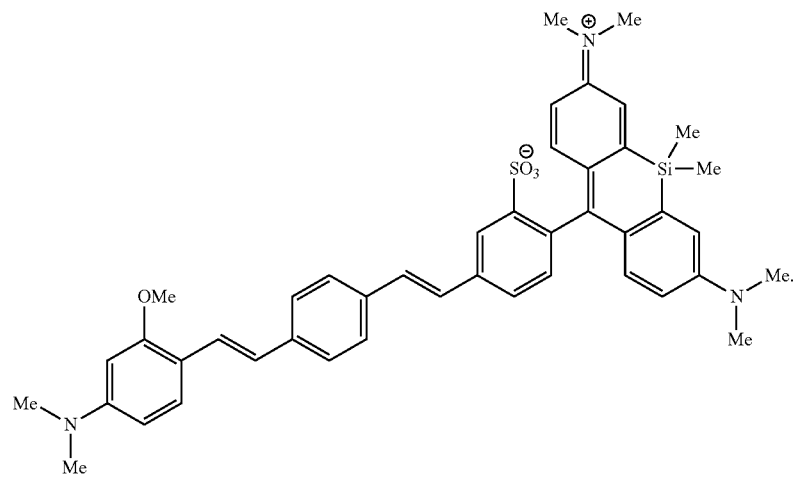

In another embodiment, a compound disclosed herein has one or more of the following characteristics: the compound emits far red to near infrared light upon excitation with incident light; the compound is water soluble; the compound exhibits minimal solvatochromism; the compound does not undergo spirocyclization in either acidic or basic environments; and/or the compound can undergo photoinduced electron transfer. In a further embodiment, a compound disclosed herein is characterized by emitting far red to near infrared light upon excitation with incident light; is water soluble; exhibits minimal solvatochromism; does not undergo spirocyclization in either acidic or basic environments; and can undergo photoinduced electron transfer.

The disclosure also provides a method to image cells, comprising: contacting the cell with a compound disclosed herein; illuminating the cells with light having a first wavelength; imaging the cells by detecting light having a second wavelength, wherein the first wavelength and second wavelength of light have different wavelengths, and wherein the light having the second wavelength is in the far red to near infrared region/wavelengths. In a further embodiment, the method further comprises: contacting the cells with one or more additional optogenetic tools; and imaging the cells by detecting light emissions at one or more additional wavelengths. Examples of optogenetic tools include, but are not limited to, GFP, $Ca^{2+}$ indicators, voltage sensors based on cpGFP, and ChannelRhodopsin2 (ChR2).

The disclosure provides a method to measure changes in membrane potential in an excitable cell comprising: contacting the excitable cell with a compound disclosed herein; stimulating the cell to evoke action potentials; and measuring action potential firing by optical or electrical sampling. In another embodiment, the optical sampling is measured using an electron multiplying charge couple device. In yet another embodiment, the excitable cell is stimulated using a whole-cell current clamp or by field stimulation. Examples of excitable cells include, but are not limited to, neurons, cardiomyocytes, myocytes, or secretory cells. In yet another embodiment, the method interrogates membrane potentials of a neuron.

In a particular embodiment, the disclosure also provides for a kit comprising: aliquots which comprise a compound disclosed herein in a buffered solution, or a concentrated solution comprising a compound disclosed herein in a buffered solution in a buffered solution that is subsequently diluted prior to use.

DESCRIPTION OF DRAWINGS

FIG. 1A-F provides for the in vitro and cellular characterization of Berkeley Red Sensor of Transmembrane potential 1 (BeRST 1). Absorbance (blue) and emission (red) spectra of (A) BeRST 1 in aqueous buffer (50 mM TBS, pH 7.5, 0.1% SDS). Excitation was provided at 635 nm. (B) Photostability of BeRST 1 and VF2.1.Cl dyes in HEK cells. Cells were loaded with 200 nM BeRST 1 or VF2.1.Cl and then illuminated continuously for 10 min at either 631 nm (BeRST 1) or 475 nm (VF2.1.Cl) at 162 W/cm². Images were acquired at 20 second intervals. The normalized fluorescence intensity from dye-loaded cells was plotted vs. time. Magenta circles represent BeRST 1-stained cells and green circles represent VF-2.1.Cl-stained cells. Error bars are standard error of mean for n=6 separate experiments. Multi-color epifluorescence imaging with BeRST 1. HEK cell were loaded with 1 µM BeRST 1, 1 µHoechst 33342, and 5 µM Rhodamine 123. (C) BeRST 1 fluorescence localized to the cell membrane, (D) Rhodamine 123 fluorescence localized to mitochondria, (E) Hoechst 33342 fluorescence localized to the nucleus, and (F) transmitted light DIC of HEK cells. Scale bar is 10 µm.

FIG. 3A-C presents epifluorescence imaging of (A,B) Berkeley Red and (C) BeRST 1 in HEK cells. (A) Cells stained with 1 µM BR and illuminated with 631 nm light (188 W/cm²) show negligible cellular fluorescence. (B) Brightening of panel (A) shows a small amount of dye internalization, with very poor contrast between intra- and extracellular space. (C) Cells stained with 1 µM BeRST 1 and illuminated at with 631 nm light (80 W/cm², 2.4× less light intensity than in panel (A)). Clear membrane staining is observed. All imaging parameters and display settings are identical for panels (A) and (C), except light intensity, which is 2.4× lower for illumination of BeRST 1. Scale bar is 20 µm.

FIG. 4A-B Voltage sensitivity of BeRST 1 in HEK cells. (A) Plot of fractional change in fluorescence (ΔF/F) vs time from BeRST 1-stained HEK cells under whole-cell, voltage-clamp conditions. Cells were held at −60 mV and stepped to hyper- or de-polarizing potentials (±100 mV) in 20 mV increments. (B) Plot of ΔF/F vs. final membrane potential. (Error bars are ±standard error of the mean for n=15 cells from 3 different cultures).

FIG. 5A-D shows action potential (AP) visualization with BeRST 1. (A) Rat hippocampal neurons were (B) stained with 1 µM BeRST 1 and field stimulated to evoke action potentials that were (C) recorded optically. Optical sampling frequency is 500 Hz, acquired with an EMCCD camera under 63× magnification. Scale bar is 10 µm. In a separate experiment, neurons were subjected to whole-cell current clamp and stimulated to induce action potential firing. Dual electrical and optical recording (1.8 kHz frame rate) are shown in panel (D). Black trace is the electrophysiological recording and red circles represent the optical response. A small stimulus artifact is apparent before and after the action potential in the black trace.

FIG. 6A-E provides a comparison of cellular electrophysiological parameters in rat hippocampal neurons loaded with either 1 µM BeRST 1 or nothing. Evoked action potentials were assessed under dye-loaded and dye-free conditions. Action potentials were averaged across n=12 and n=11 cells for unloaded neurons and neurons loaded with 1 µM BeRST 1. No statistically significant differences across a number of electrophysiological parameters, including (A) peak action potential amplitude, (B) action potential duration as measured by full width at half-max, (C) cellular capacitance, (D) rise time, or (E) decay time. Unpaired t-tests, p>0.5. Error bars are SEM.

FIG. 7A-H shows imaging evoked activity in GFP-positive rat hippocampal neurons with BeRST 1. Action potentials from neurons expressing (A) GFP and stained with (B) BeRST 1 were evoked via field stimulation and recorded (C-H) in the regions of interest indicated in panels (A) and (B). Stimulation was provided at 5 Hz and optically recorded at 500 Hz.

FIG. 9A-E provides dual voltage and $Ca^{2+}$ imaging with BeRST 1 and GCaMP6s. Epifluorescence images of a rat hippocampal neuron stained (A) with BeRST 1 and expressing (B) GCaMP6s. Scale bar is 20 µm. (C) Sequential $Ca^{2+}$ and voltage imaging during field stimulation of the neuron in panels (A) and (B). Voltage—(upper) and $Ca^{2+}$—(lower) induced changes in fluorescence. (D) Voltage—(left) and (E) $Ca^{2+}$—(right) induced fluorescence response to trains of action potentials at the indicated frequency. Optical sample rate is 500 Hz for BeRST 1 and 40 Hz for GCaMP6s.

FIG. 10A-F presents two-color voltage imaging with genetically encoded voltage-fluorescent proteins and small molecule voltage-sensitive dyes. Epifluorescence images of rat hippocampal neurons (A) stained with BeRST 1 and (B) expressing the voltage-sensitive fluorescent protein ASAP1. Zoomed-in region for functional imaging of voltage via (C) BeRST 1 staining or (D) ASAP1 fluorescence. The magnified regions correspond to the white boxes in panels (A) and (B). All scale bars are 20 µm. Trains of action potentials evoked by field stimulation at 5 Hz detected by changes in (E) BeRST 1 fluorescence (upper trace) or ASAP1 fluorescence (lower trace). (F) A single action potential, magnified from panel (E). Magenta is BeRST 1 and green is ASAP1 fluorescence. The optical sampling rate was 1.25 kHz. Traces are background corrected, but not bleach-corrected.

FIG. 11A-E provides cross excitation of BeRST 1 in rat hippocampal neurons. Panels A-C represent the same field of neurons from a culture loaded with 1 µM BeRST 1 and excited at (A) 631 nm, (B) 475 nm, or (C) 390 nm (9.7 W/cm² for all wavelengths). Scale bar is 20 µm. (D) The relative emission intensity at 680 nm is quantified for each excitation condition. Error bars are ±SEM for n=5 separate cells. (E) Voltage sensitivity of neurons stained with BeRST 1 when excited at 631 nm (6.7 W/cm²) or 390 nm (3.3 W/cm²) light. Fractional changes in fluorescence are calculated to be 26% and 28% ΔF/F per 100 mV for 631 nm and 390 nm excitation, respectively (n=4 separate cells).

FIG. 13A-F provides for optical electrophysiology with BeRST 1 and ChR2. Epifluorescence images of rat hippocampal neurons expressing (A) YFP-ChR2 and (B) stained with BeRST 1. Inset on panel (B) is the region inscribed by the dotted white box. The inset image is single frame used to acquire data for panels (D) and (F). Scale bars are 20 µm (panel A/B) and 10 µm (panel (B), inset). Simultaneous (C) electrophysiological and (D) optical recording of membrane potential changes evoked by optogenetic stimulation of the neuron expressing YFP-ChR2 and stained with BeRST 1. Cyan light (475 nm LED, 80 mW/cm²) was provided in 5 ms pulses at a rate of 5 Hz. Magnified view of (E) electrophysiological and (F) optical recording of the action potential highlighted in the red, dotted box from panels (C) and (D). Optical sampling rate was 1 kHz. Optical traces are background corrected, but not bleach-corrected.

FIG. 14A-E All-optical electrophysiology with BeRST 1 and ChR2. Epifluorescence images of rat hippocampal neurons stained with (A) BeRST 1 and expressing (B) YFP-ChR2. (C) Magnified view of white box in panel (A). This image is a single frame used to acquire data for panels (D) and (E). Scale bars are 20 µm. Optical (upper) and electrophysiological (lower) responses to optogenetic stimulation of the neuron in panels (A-C) with 5 ms pulse of cyan light (475 nm, 0.08 W/cm²) at a rate of (D) 10 Hz or (E) 5 Hz. Electrophysiological recordings were acquired at a sampling rate of 20 kHz in cell-attached patch clamp configuration. Optical traces acquired at 1 kHz were not corrected for bleaching.

FIG. 15A-G provides for using BeRST 1 and ChR2 to perturb network activity. Cultured rat hippocampal (C) neurons transfected with (A) YFP-ChR2 and stained with (B) BeRST 1 were stimulated with 475 nm light (80 mW/cm², 5 ms, 5 Hz, cyan bars) during two separate 3 second periods to evoke activity in the YFP-ChR2-expressing cell. Scale bar is 20 µm. (D) Schematic representation of neurons from DIC image in panel (C), color-coded to match the corresponding traces in (E-G). The blue ChR2⁺ cell is depicted making possible connections to other neurons in the field of view. Optical records of BeRST 1 responses were acquired at 500 Hz with an sCMOS camera during (E) an optical recording session and (F) subsequent trial, separated by approximately 30 seconds (double hash). Numbers and colors of traces refer to specific neurons in panels (A-D). Red boxes indicate areas of the trace that have been magnified for clarity in panel (G). Dotted grey lines are provided in panel (G) to help visually estimate the spike timing of BeRST 1-stained neurons.

FIG. 16 presents neuron expressing YFP-ChR2. Scale bar is 20 µm. Total image area is 665×665 µm. Dashed box indicates approximate imaging area from FIG. 15.

FIG. 17 shows the $^1H$ NMR of 2,5-dibromo-benzenesulfonic acid isopropyl ester.

FIG. 25 shows the HPLC traces of BeRST 1 at 254 and 650 nm.

FIG. 26 shows the $^1H$ NMR spectrum organolithium reagent derived from 2,5-dibromo-benzenesulfonic acid isopropyl ester, following quenching with H⁺ (crude reaction mixture).

DETAILED DESCRIPTION

Figure 2A:
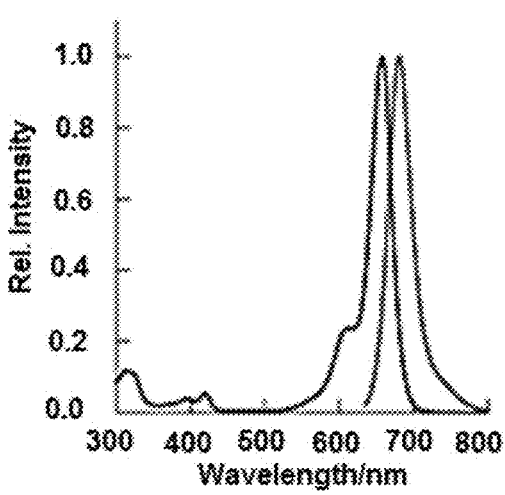
FIG. 2A-E shows the spectroscopic characterization of Berkeley Red. (A) Absorbance (blue) and emission (red) spectrum of BR in aqueous buffer. UV-vis spectrum of BR at (B) various dielectric constant (achieved by mixtures of dioxane/water ranging from 10 to 90%) or (C) pH (ranging from 2.5 to 9). Plot of relative absorbance of BR vs. (D) dielectric constant and (E) pH.

As used herein and in the appended claims, the singular forms "a," "and," and "the" include plural referents unless the context clearly dictates otherwise. Thus, for example, reference to "a fluorophore" includes a plurality of such fluorophores and reference to "the voltage sensitive dye" includes reference to one or more voltage sensitive dyes or equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in their entirety for the purposes of describing and disclosing methodologies that might be used in connection with the description herein. Moreover, with respect to any term that is presented in the publications that is similar to, or identical with, a term that has been expressly defined in this disclosure, the definition of the term as expressly provided in this disclosure will control in all respects.

Unless defined otherwise, all technical and scientific terms used herein have the same meaning as commonly understood by one of ordinary skill in the art to which this disclosure belongs. Although many methods and reagents similar to or equivalent to those described herein can be used in the practice of the disclosed methods and compositions, the exemplary methods and materials are now described.

The term "alkyl", refers to an organic group that is comprised of carbon and hydrogen atoms that contain single covalent bonds between carbons. Typically, an "alkyl" as used in this disclosure, refers to an organic group that contains 1 to 30 carbon atoms, unless stated otherwise. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkenyl", refers to an organic group that is comprised of carbon and hydrogen atoms that contains at least one double covalent bond between two carbons. Typically, an "alkenyl" as used in this disclosure, refers to organic group that contains 1 to 30 carbon atoms, unless stated otherwise. While a $C_1$-alkenyl can form a double bond to a carbon of a parent chain, an alkenyl group of three or more carbons can contain more than one double bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains 1 to 30 carbon atoms, unless stated otherwise. While a $C_1$-alkynyl can form a triple bond to a carbon of a parent chain, an alkynyl group of three or more carbons can contain more than one triple bond. Where if there is more than 1 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompass from 1 to 12 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "cylcloalkenyl", as used in this disclosure, refers to an alkene that contains at least 3 carbon atoms but no more than 12 carbon atoms connected so that it forms a ring. A "cycloalkenyl" for the purposes of this disclosure encompass from 1 to 12 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "aryl", as used in this disclosure, refers to a conjugated planar ring system with delocalized pi electron clouds that contain only carbon as ring atoms. An "aryl" for the purposes of this disclosure encompass from 1 to 12 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term "heterocycle", as used in this disclosure, refers to ring structures that contain at least 1 non-carbon ring atom. A "heterocycle" for the purposes of this disclosure encompass from 1 to 12 heterocycle rings wherein when the heterocycle is greater than 1 ring the heterocycle rings are joined so that they are linked, fused, or a combination thereof. A heterocycle may be a hetero-aryl or nonaromatic, or in the case of more than one heterocycle ring, one or more rings may be nonaromatic, one or more rings may be hetero-aryls, or a combination thereof. A heterocycle may be substituted or unsubstituted, or in the case of more than one heterocycle ring one or more rings may be unsubstituted, one or more rings may be substituted, or a combination thereof. Typically, the non-carbon ring atom is N, O, S, Si, Al, B, or P. In case where there is more than one non-carbon ring atom, these non-carbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1] heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "hetero-" when used as a prefix, such as, hetero-alkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and O.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "unsubstituted" with respect to hydrocarbons, heterocycles, and the like, refers to structures wherein the parent chain contains no substituents.

The term "substituted" with respect to hydrocarbons, heterocycles, and the like, refers to structures wherein the parent chain contains one or more substituents.

The term "substituent" refers to an atom or group of atoms substituted in place of a hydrogen atom. For purposes of this disclosure, a substituent would include deuterium atoms.

The term "hydrocarbons" refers to groups of atoms that contain only carbon and hydrogen. Examples of hydrocarbons that can be used in this disclosure include, but are not limited to, alkanes, alkenes, alkynes, arenes, and benzyls.

The term "functional group" or "FG" refers to specific groups of atoms within molecules that are responsible for the characteristic chemical reactions of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Examples of FG that can be used in this disclosure, include, but are not limited to, substituted or unsubstituted alkyls, substituted or unsubstituted alkenyls, substituted or unsubstituted alkynyls, substituted or unsubstituted aryls, substituted or unsubstituted hetero-alkyls, substituted or unsubstituted hetero-alkenyls, substituted or unsubstituted hetero-alkynyls, substituted or unsubstituted cycloalkyls, substituted or unsubstituted cycloalkenyls, substituted or unsubstituted hetero-aryls, substituted or unsubstituted heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, $Si(OH)_3$, $Ge(OH)_3$, $Sn(OH)_3$, $Si(SH)_4$, $Ge(SH)_4$, $AsO_3H$, $AsO_4H$, $P(SH)_3$, $As(SH)_3$, $SO_3H$, $Si(OH)_3$, $Ge(OH)_3$, $Sn(OH)_3$, $Si(SH)_4$, $Ge(SH)_4$, $Sn(SH)_4$, $AsO_3H$, $AsO_4H$, $P(SH)_3$, $SO_2$, $SO_3^-$ and $As(SH)_3$.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

Rapid changes in the membrane potential ($V_{mem}$) of excitable cells like neurons and cardiomyocytes play a central role in defining cellular signaling and physiological profiles of these specialized cells. Classically, $V_{mem}$ is monitored and measured via patch clamp electrophysiology, in which a microelectrode attached to the cell of interest enables highly sensitive recordings of membrane voltage with exquisite temporal resolution. However, the use of electrodes is highly invasive, limits records to the soma of a single cell (space clamp error), and is extremely low throughput. Optical techniques for recording voltage represent a feasible solution to these problems, because they are minimally invasive, requiring delivery of a sensor and photons, and can be high throughput. $Ca^{2+}$ imaging has long been used a surrogate for direct optical measurement of voltage, in part because the robust imaging agents, whether based on small molecules or on fluorescent proteins, are sensitive, applicable to a wide range of biological contexts, and come in a variety of colors. The use of $Ca^{2+}$ imaging provides only an imperfect approximation of $V_{mem}$ changes, since intracellular $[Ca^{2+}]0$ ($[Ca^{2+}]_i$) rises are triggered by the depolarization of $V_{mem}$. Additionally, because $[Ca^{2+}]_i$ transients last for hundreds of milliseconds and because the $Ca^{2+}$ sensors themselves can buffer the rise and fall of $[Ca^{2+}]_i$, resolving fast spiking neuronal events becomes impossible or difficult, requiring extensive deconvolution protocols.

Direct voltage imaging, therefore, is attractive, because it can provide a direct readout of $V_{mem}$ while still achieving the spatial resolution, high throughput and minimal invasiveness of $Ca^{2+}$ imaging. Recently, there has been renewed interest in the development fluorescent voltage sensors, through the use of small molecules, fluorescent proteins, combinations of the two, or opsins.

The voltage sensitive dyes disclosed herein possess excitation and emission profiles in the NIR window, which allows for the integration of the compounds disclosed herein with other optical tools. For example, depolarization of the plasma membrane results in rapid increases in NIR fluorescence for the compounds disclosed herein (e.g., ≥24% ΔF/F per 100 mV). Additionally, for imaging in thicker biological samples like tissue slices or whole animals, NIR excitation and emission profiles (650 to 900 nm) are desirable because lower energy photons reduce tissue damage, scatter less, are absorbed by fewer endogenous chromophores, and produce lower levels of autofluorescence. In direct contrast, Voltage-Fluors, or VF dyes, a small molecule platform for voltage sensing that relies on photoinduced electron transfer (PeT) modulated by changes in $V_{mem}$ are significantly limited by having an excitation and emission profile that lies in the blue/green region of the electromagnetic spectrum. Because these VF dyes are excited in the 480 to 515 nm range and emit around 530 nm, their emission significantly overlap with a number of useful optical tools, such as GFP, robust $Ca^{2+}$ sensors like Oregon Green BAPTA and the GCaMP family, and optogenetic tools like ChannelRhodopsin2 (ChR2). Accordingly, the compounds disclosed herein avoid the drawbacks associated with imaging at shorter wavelengths using VF dyes or other compounds.

Moreover, the compounds of the disclosure can be used with fluorescent stains for organelles, $Ca^{2+}$ indicators, and voltage-sensitive fluorescent proteins; and can be used in conjunction with optogenetic actuators like ChannelRhodopsin2 (ChR2) (which utilizes blue light), the red-shifted spectral profile of the compounds of the disclosure enable optical electrophysiology in neurons.

The disclosure thus describe the design, synthesis, and characterization of dye compounds for use in voltage sensing applications. The compounds of the disclosure display bright, membrane-localized fluorescence, is highly photostable, and extremely voltage-sensitive. The compounds can detect action potentials in, for example, cultured hippocampal neurons and interface readily with a number of other optical tools. According, the compounds of the disclosure are ideally suited for multicolor imaging with GFP, $Ca^{2+}$ indicators like GCaMP, voltage sensors based on cpGFP such as ASAP1, as well as optogenetic tools like ChR2. Use of the compounds of the disclosure alongside ChR2 permits non-invasive recording and control of membrane potential in single cells and in neuronal microcircuits.

Molecular probes comprising the compounds of the disclosure fill an important role in measuring membrane potential, as the compounds of the disclosure do not require any genetic manipulation, can be delivered to all cell types, respond rapidly to fast voltage changes, and can be tuned across a wide color range. Further, in certain embodiments disclosed herein, the compounds may further comprise a phenylenevinylene molecular wire based platform. The emission profile of the compounds disclosed herein can therefore be tuned based upon structural modification of the molecular wire platform or by making minor changes to the fluorophore. Accordingly, the compounds of the disclosure are invaluable tools for mapping membrane potential dynamics in a variety of systems.

In one embodiment, the disclosure provides for a compound having the structure of Formula I:

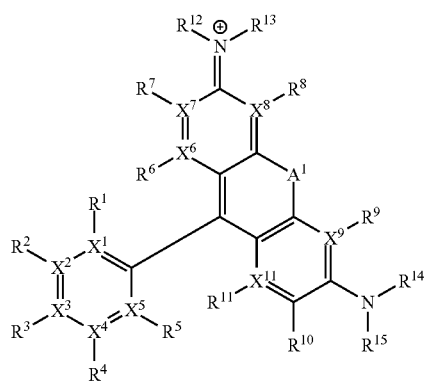

Formula I wherein, $A^1$ is selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$)alkyl, optionally substituted ($C_1$-$C_{11}$)heteroalkyl, optionally substituted ($C_1$-$C_{12}$) alkenyl, optionally substituted ($C_1$-$C_{11}$)heteroalkenyl, optionally substituted ($C_1$-$C_{12}$)alkynyl, and optionally substituted ($C_1$-$C_{11}$)heteroalkynyl;

$X^1$-$X^{11}$ are independently selected from N or C, wherein when an X group is an N, then the R group is absent; and $R^1R^{15}$ are independently selected from H, D, optionally substituted FG, optionally substituted ($C_1$-$C_{12}$)alkyl, optionally substituted ($C_1$-$C_{11}$)heteroalkyl, optionally substituted ($C_1$-$C_{12}$)alkenyl, optionally substituted ($C_1$-$C_{11}$)heteroalkenyl, optionally substituted ($C_1$-$C_{12}$)alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In a further embodiment, at least one of $R^1$ to $R^5$ of Formula II is a sulfonate group.

In another embodiment, the disclosure provides for a compound having the structure of Formula I(a):

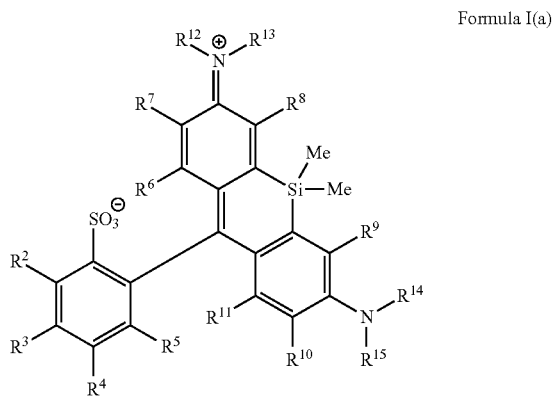

Formula I(a)

wherein, $R^2$-$R^{15}$ are independently selected from H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, optionally substituted ($C_1$-$C_5$)heteroalkynyl, optionally substituted ($C_5$-$C_7$)cycloalkyl, optionally substituted ($C_5$-$C_7$)cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system.

In yet a further embodiment, the disclosure provides for a compound having the structure of:

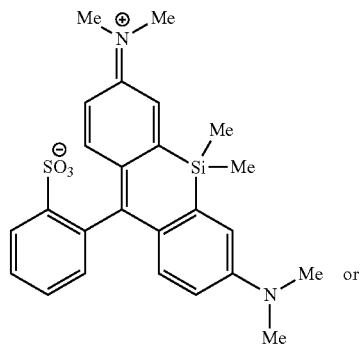

or

-continued

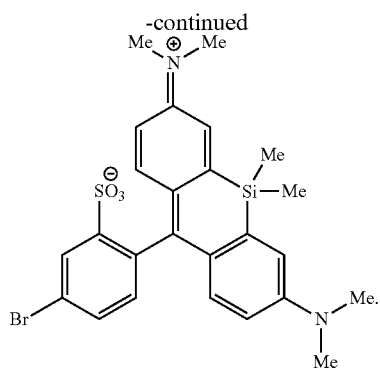

In yet another embodiment, the disclosure provides for a compound having the structure of Formula II:

Formula II

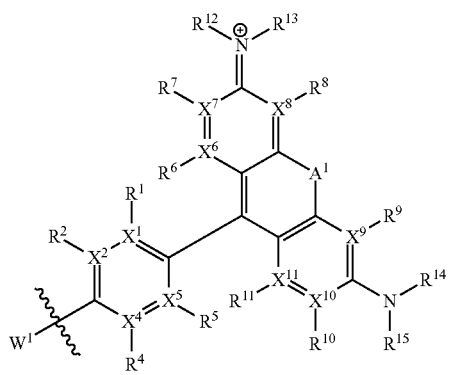

wherein,

A$^1$ is selected from CH$_2$, CHR', CR'$_2$, NH, O, S, Se, Te, SiH$_2$, SiHR', SiR'$_2$, GeH$_2$, GeHR', GeR'$_2$, SnH$_2$, SnHR', SnR'$_2$, PbH$_2$, PbHR', or PbHR'$_2$, wherein R' is selected from the group consisting of D, optionally substituted FG, optionally substituted (C$_1$-C$_{12}$)alkyl, optionally substituted (C$_1$-C$_{11}$)heteroalkyl, optionally substituted (C$_1$-C$_{12}$) alkenyl, optionally substituted (C$_1$-C$_{11}$)heteroalkenyl, optionally substituted (C$_1$-C$_{12}$)alkynyl, and optionally substituted (C$_1$-C$_{11}$)heteroalkynyl;

W$^1$ is a molecular wire moiety;

X$^1$, X$^2$, and X$^4$-X$^{11}$ are independently selected from N or C, wherein when an X group is an N, then R group is absent;

R$^1$, R$^2$, and R$^4$-R$^{15}$ are independently selected from H, D, optionally substituted FG, optionally substituted (C$_1$-C$_{12}$) alkyl, optionally substituted (C$_1$-C$_{11}$)heteroalkyl, optionally substituted (C$_1$-C$_{12}$)alkenyl, optionally substituted (C$_1$-C$_{11}$) heteroalkenyl, optionally substituted (C$_1$-C$_{12}$)alkynyl, optionally substituted (C$_1$-C$_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system. In a further embodiment, at least one of R$^1$, R$^2$, R$^4$, and R$^5$ is a sulfonate group.

In one embodiment, the disclosure also provides for a compound comprising the structure of Formula II(a):

Formula II (a)

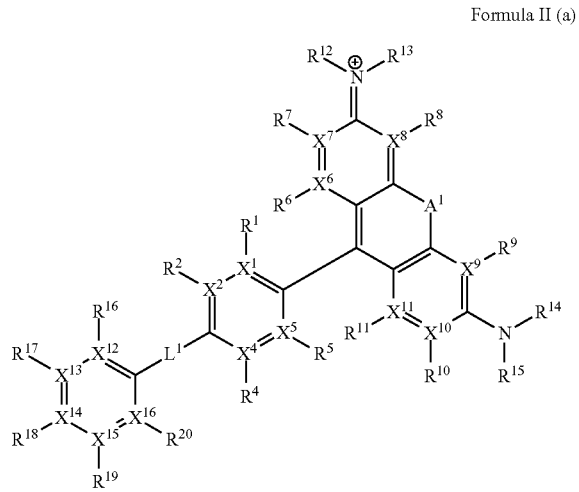

wherein,

L$^1$ is selected from the group consisting of:

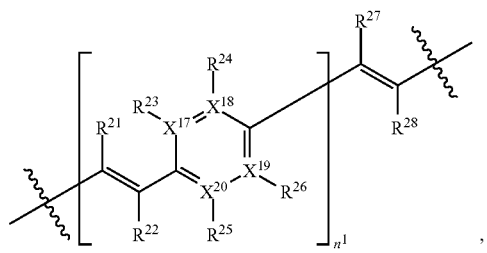

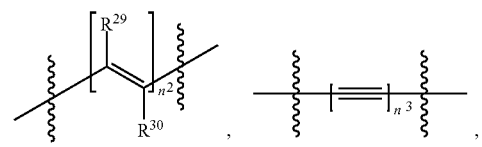

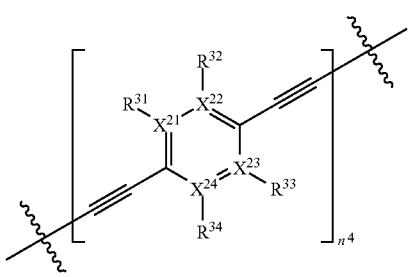

-continued

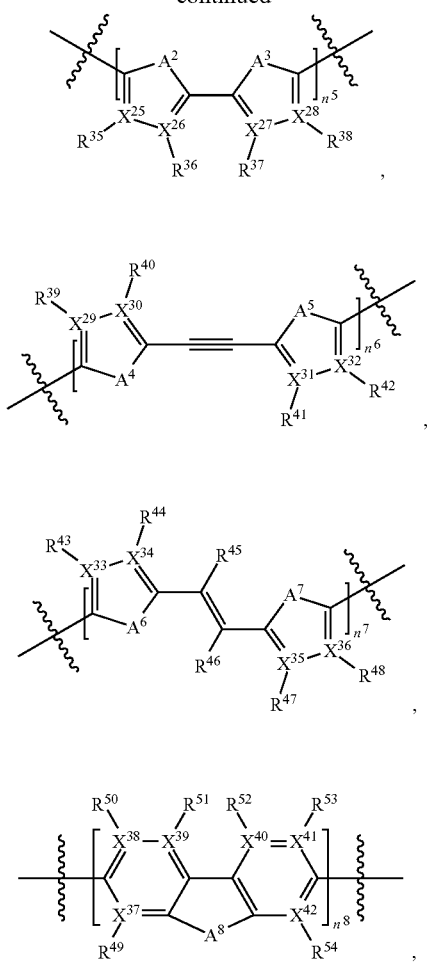

and any combination of the foregoing;

$A^1$-$A^8$ are each independently selected from $CH_2$, CHR', $CR'_2$, NH, O, S, Se, Te, $SiH_2$, SiHR', $SiR'_2$, $GeH_2$, GeHR', $GeR'_2$, $SnH_2$, SnHR', $SnR'_2$, $PbH_2$, PbHR', or $PbHR'_2$, wherein R' is selected from the group consisting of D, optionally substituted FG, optionally substituted ($C_1$-$C_{12}$) alkyl, optionally substituted ($C_1$-$C_{11}$) heteroalkyl, optionally substituted ($C_1$-$C_{12}$)alkenyl, optionally substituted ($C_1$-$C_{11}$) heteroalkenyl, optionally substituted ($C_1$-$C_{12}$)alkynyl, and optionally substituted ($C_1$-$C_{11}$)heteroalkynyl;

$X^1$, $X^2$, and $X^4$-$X^{42}$ are independently selected from N or C, wherein when an X group is an N, then the R group is absent;

$R^1$, $R^2$, and $R^4$-$R^{54}$ are independently selected from H, D, optionally substituted FG, optionally substituted ($C_1$-$C_{12}$) alkyl, optionally substituted ($C_1$-$C_{11}$)heteroalkyl, optionally substituted ($C_1$-$C_{12}$) alkenyl, optionally substituted ($C_1$-$C_{11}$) heteroalkenyl, optionally substituted ($C_1$-$C_{12}$)alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and $n^1$-$n^8$ are independently an integer selected from 0 to 10.

In a further embodiment, at least one of $R^1$, $R^2$, $R^3$ and $R^4$ is a sulfonate group.

In another embodiment, the disclosure provides for a compound comprising the structure of Formula II(b):

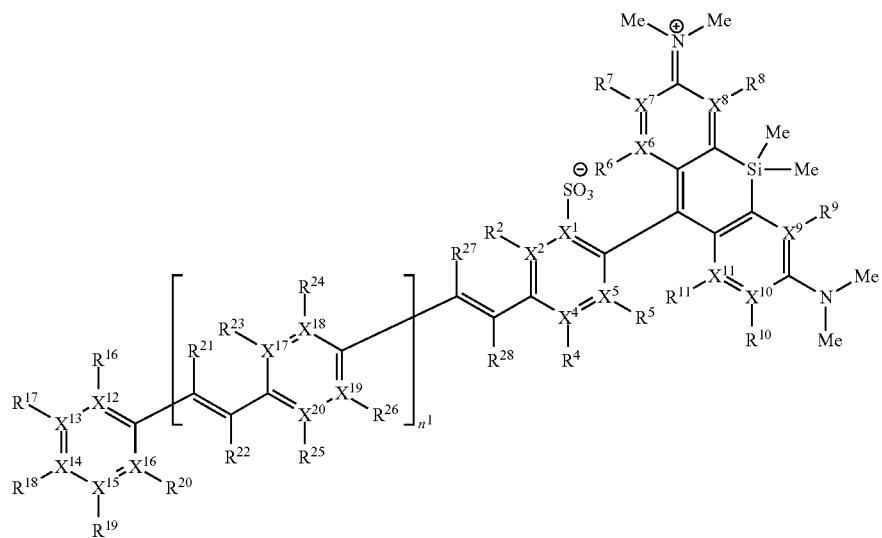

Formula II (b)

wherein, $X^1$, $X^2$, and $X^4$-$X^{20}$ are independently selected from N or C, wherein when an X group is an N, then the R group is absent;

$R^2$, $R^4$-$R^{11}$, and $R^{16}$-$R^{26}$ are independently selected from H, D, optionally substituted FG, optionally substituted ($C_1$-$C_6$)alkyl, optionally substituted ($C_1$-$C_5$)heteroalkyl, optionally substituted ($C_1$-$C_6$) alkenyl, optionally substituted ($C_1$-$C_5$) heteroalkenyl, optionally substituted ($C_1$-$C_6$)alkynyl, optionally substituted ($C_1$-$C_5$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system; and n is an integer from 1 to 5.

In another embodiment, the disclosure provides for a compound having the structure of Formula II(c):

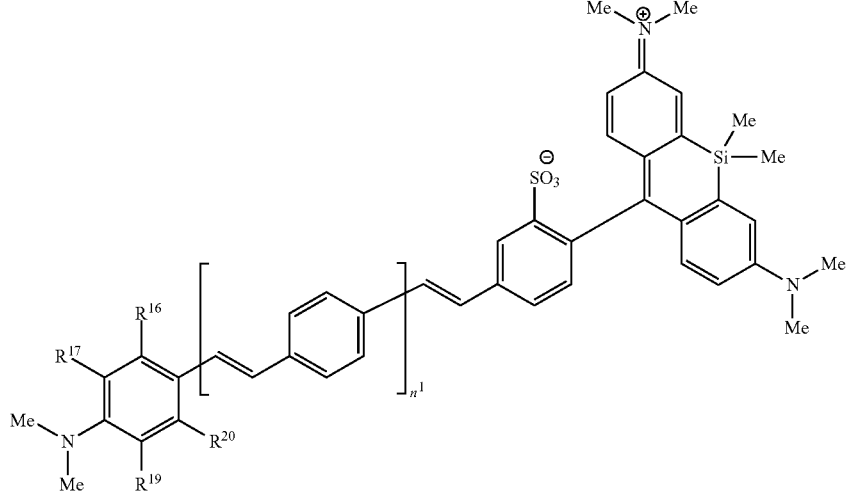

Formula II (c)

wherein, $R^{16}$, $R^{17}$, $R^{19}$ and $R^{20}$ are independently selected from H, D, optionally substituted FG, optionally substituted ($C_1$-$C_6$) alkyl, optionally substituted ($C_1$-$C_5$)heteroalkyl, optionally substituted ($C_1$-$C_6$) alkenyl, optionally substituted ($C_1$-$C_5$) heteroalkenyl, optionally substituted ($C_1$-$C_6$)alkynyl, optionally substituted ($C_1$-$C_5$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system;

n is an integer from 0 to 5.

In yet another embodiment, the disclosure provides for a compound having the structure of:

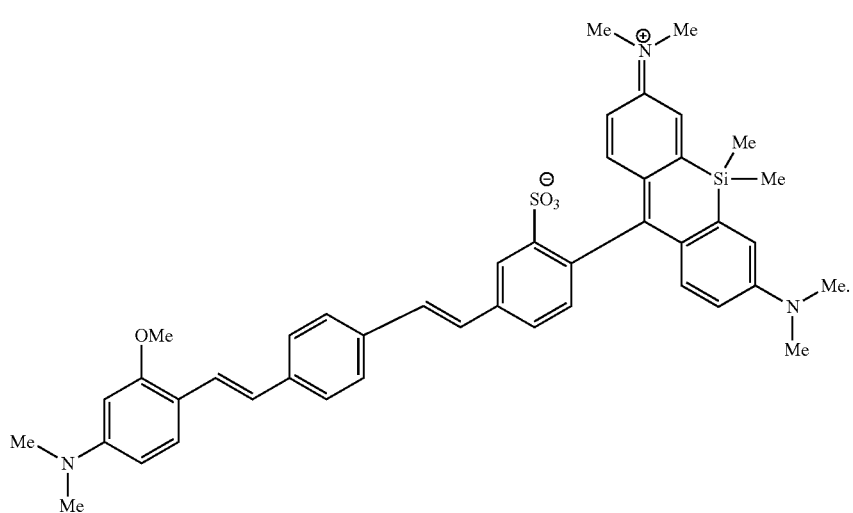

Formula III

It should be further noted, that for any structure depicted herein (e.g., Formula I, I(a), II, II(a), III) that any resonance form of the foregoing structures is further contemplated herein. For example, a compound having the structure of Formula III would include the resonance structures of:

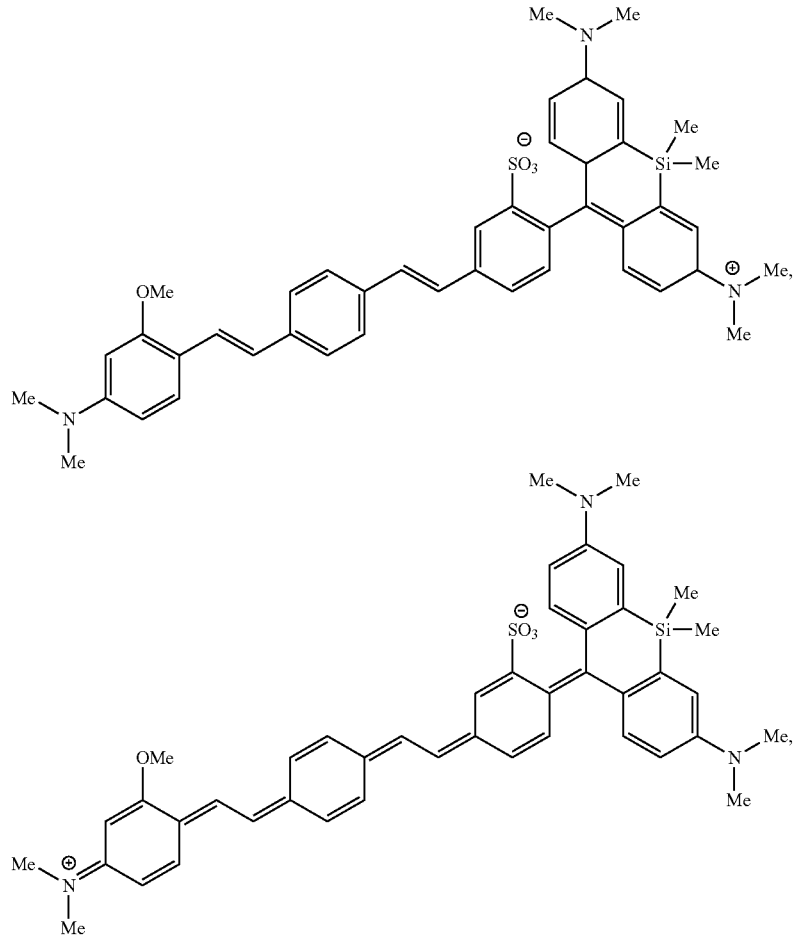

etc.

It should be further understood, that while the formulae depicted herein are indicated as having charged species, the uncharged species are also contemplated herein. Accordingly, the formulae should be viewed as providing for uncharged groups in addition to the depicted positively charged nitrogens and negatively charged sulfur groups.

In a certain embodiments described herein, the compounds of the disclosure are characterized by being voltage sensitive and emit light in the near-infra red (NIR) region upon excitation with incident light. Advantages of the compounds described herein include minimal interfering absorption and fluorescence from biological samples, inexpensive laser diode excitation, and reduced scattering and enhanced tissue penetration depth. In another embodiment, the compounds depicted herein are further characterized by being water soluble and/or exhibiting minimal solvatochromism.

In a particular embodiment, the disclosure provides for a sensor comprising a compound disclosed herein for interrogating membrane potential dynamics in neurons. In yet a further embodiment, the sensor is triggered by photoinduced electron transfer (PeT).

In a certain embodiment, the disclosure provides methods for using the compounds disclosed herein, comprising exciting the compound with incident light; measuring the emission of far red to near infrared light by the compound. In a further embodiment, light emitted by the compound at 650 to 800 nm is quantitated. In yet a further embodiment, light emitted by the compound at 650 nm to 685 nm is quantitated. In another embodiment, the compound can be excited by exposing the compound to incident light having a wavelength from 380 nm to 640 nm. In yet another embodiment, the incident light has a wavelength around 630 nm or about 390 nm. In particular embodiments, the compounds disclosed herein can be used in methods for cell imaging, drug screening and voltage sensing. In a further embodiment, the compounds are ideally suited for interrogating membrane potential dynamics in neurons. In yet a further embodiment, the compounds disclosed herein are useful for screening drugs that affect membrane potential/ion channels or for screening drug safety and/or efficacy.

The disclosure provides methods for screening test samples such as potential therapeutic drugs which affect membrane potentials in biological cells. These methods involve measuring membrane potentials in the presence and absence (control measurement) of a test sample or agent. Control measurements are usually performed with a sample containing all components of the test sample except for the putative drug. Detection of a change in membrane potential in the presence of the test agent relative to the control indicates that the test agent is active. Membrane potentials can be also be determined in the presence or absence of a pharmacologic agent of known activity (i.e., a standard agent) or putative activity (i.e., a test agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials. Use of the membrane potential determination technique disclosed herein in combination with all such methods are contemplated by this disclosure.

In a particular application, the disclosure provides a method of identifying a compound which modulates activity of an ion channel, pump, or exchanger in a membrane, comprising: (a) loading the cells with a compound (i.e., a voltage sensitive dye) of the disclosure, which measure membrane potential as described herein; (b) determining the membrane potential; (c) exposing the cells to the test sample/agent; (d) redetermining the membrane potential and comparing with the result in (b) to determine the effect of the test sample; (e) optionally, exposing the membrane to a stimulus which modulates an ion channel, pump or exchanger, and redetermining the membrane potential and comparing with the result in (d) to determine the effect of the test sample on the response to the stimulus.

As used herein, an ion channels includes, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, cells dissociated from mammalian tissue, either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The disclosure also includes the use of recombinant cells into which ion transporters, ion channels, pumps and exchangers have been inserted and expressed by genetic engineering. The cells are typically mammalian cell such as L-M (TK-) cells, neuroblastoma cells, astrocytoma cells and neonatal cardiac myocytes.

The screening methods described herein can be made on cells growing in or deposited on solid surfaces. A common technique is to use a microtiter plate well wherein the fluorescence measurements are made by commercially available fluorescent plate readers. The disclosure includes high throughput screening in both automated and semiautomated systems.

The term "membrane potential modulator" refers to components capable of altering the resting or stimulated membrane potential of a cellular or subcellular compartment. The term includes discrete compounds, ion channels, receptors, pore forming proteins or any combination of these components.

Kits are also a feature of this disclosure. Embodiments of the kits include at least one compound according to any one of general formulas described herein. Such kits are suitable for voltage sensing applications based upon photoinduced electron transfer. In other embodiments, such kits are suitable for drug screening (e.g., screening drugs that affect membrane potential/ion channels or screening for drug safety and efficacy). In some embodiments, the kits also include at least one buffer solution in which the compound, when used in conjunction with excitable cells, will allow for sensing changes in the membrane potential of the excitable cell. Alternatively, the buffer may be provided as a concentrated solution, which is subsequently diluted prior to use. In certain embodiments, the compound may be premeasured into one or more containers (e.g., test tubes or cuvettes), and the detection is subsequently performed by adding the buffer and test sample to the container.

The kits also may include one or more containers, such as a disposable test tube or cuvette, in which the detection can be performed. The kits may further include instructions for performing the detection.

The following examples are intended to illustrate but not limit the disclosure. While they are typical of those that might be used, other procedures known to those skilled in the art may alternatively be used.

EXAMPLES

General Method for Chemical Synthesis and Characterization

Chemical reagents and solvents (dry) were purchased from commercial suppliers and used without further purification. All reactions were carried out in oven-dried flasks under $N_2$. Thin layer chromatography (TLC) (Silicycle, F254, 250 µm) and preparative thin layer chromatography (PTLC) (Silicycle, F254, 1000 µm) were performed on glass backed plates pre-coated with silica gel were visualized by fluorescence quenching under UV light. Flash column chromatography was performed on Silicycle Silica Flash F60 (230-400 Mesh) using a forced flow of air at 0.5-1.0 bar. NMR spectra were measured on Bruker AVB-400 MHz, 100 MHz, AVQ-400 MHz, 100 MHz, Bruker AV-600 MHz, 150 MHz. NMR spectra measured on Bruker AVII-900 MHz, 225 MHz, equipped with a TCI cryoprobe accessory. Chemical shifts are expressed in parts per million (ppm) and are referenced to $CDCl_3$ 7.26 ppm, 77.0 ppm. Coupling constants are reported as Hertz (Hz). Splitting patterns are indicated as follows: s, singlet; d, doublet; sep, septet dd, doublet of doublet; ddd, doublet of double of doublet; dt, doublet of triplet; td, triplet of doublet; and m, multiplet. High-resolution mass spectra (ESI EI) were measured by the QB3/Chemistry mass spectrometry service at University of California, Berkeley. High performance liquid chromatography (HPLC) and low resolution ESI Mass Spectrometry were performed on an Agilent Infinity 1200 analytical instrument coupled to an Advion CMS-L ESI mass spectrometer. Columns used for the analytical HPLC was Phenomenex Luna C18(2) (4.6 mm I.D.×150 mm) with flow rates 1.0 mL/min. The mobile phase were MQ-$H_2O$ with 0.05% formic acid (eluent A) and HPLC grade acetonitrile with 0.05% formic acid (eluent B). Signals were monitored at 254 and 650 nm in 20 min with gradient 10-100% eluent B.

Spectroscopic Studies

Stock solutions of BR and BeRST 1 were prepared in DMSO (1.0-10 mM) and diluted with TBS (50 mM Tris-HCl, pH 7.5, 0.15 M NaCl) solution containing 0.10% (w/w) SDS (1:100 to 1:1000 dilution). UV-Vis absorbance and fluorescence spectra were recorded using a Shimadzu 2501 Spectrophotometer (Shimadzu) and a Quantamaster Master 4 L-format scanning spectrofluorometer (Photon Technologies International). The fluorometer is equipped with an LPS-220B 75-W xenon lamp and power supply, A-1010B lamp housing with integrated igniter, switchable 814 photon-counting/analog photomultiplier detection unit, and MD5020 motor driver. Samples were measured in 1-cm path length quartz cuvettes (Starna Cells). Relative quantum yields were measured in TBS solution containing 0.10% (w/w) SDS or in $CH_3OH$ and referenced to cresyl violet in $CH_3OH$, which has a quantum yield of 0.54.

Cell Culture

Human embryonic kidney 293T (HEK) cells were passaged and plated onto 12 mm glass coverslips pre-coated with Poly-D-Lysine (PDL; 1 mg/mL; Sigma-Aldrich) to provide a confluency of ~15% and 50% for electrophysiology and imaging, respectively. HEK cells were plated and maintained in Dulbecco's modified eagle medium (DMEM) supplemented with 4.5 g/L D-glucose, 10% FBS and 1% Glutamax.

Hippocampi were dissected from embryonic day 18 Sprague Dawley rats (Charles River Laboratory) in cold sterile HBSS (zero $Ca^{2+}$, zero $Mg^{2+}$). All dissection products were supplied by Invitrogen, unless otherwise stated. Hippocampal tissue was treated with trypsin (2.5%) for 15 min at 37° C. The tissue was triturated using fire polished Pasteur pipettes, in minimum essential media (MEM) supplemented with 5% fetal bovine serum (FBS; Thermo Scientific), 2% B-27, 2% 1M D-glucose (Fisher Scientific) and 1% glutamax. The dissociated cells were plated onto 12 mm diameter coverslips (Fisher Scientific) pre-treated with PDL (as above) at a density of 30,000-40,000 cells per coverslip in MEM supplemented media (as above). Neurons were maintained at 37° C. in a humidified incubator with 5% $CO_2$. At 3 days in vitro (DIV) half of the MEM supplemented media was removed and replaced with Neurobasal media containing 2% B-27 supplement and 1% glutamax. Transfection of genetic tools was carried out using Lipofectamine 3000 at 7 DIV. Functional imaging was performed on mature neurons 13-20 DIV, except electrophysiological experiments which were performed on 12-15 DIV neurons.

Unless stated otherwise, for loading of HEK cells and hippocampal neurons, BeRST 1 was diluted in DMSO to 1 mM, and then diluted 1:1000 in HBS (in mM) 140 NaCl, 2.5 KCl, 10 HEPES, 10 D-glucose 1.3 $MgCl_2$ and 2 CaCl2; pH 7.3 and 290 mOsmol. All imaging experiments were performed in HBS.

DNA Constructs

Constructs used in the experiments described herein include, channelrhodopsin-2-YFP (ChR2-YFP), puro-CAG-ASAP1 and GCaMP6s. CHR2-YFP drives neuronal expression of channelrhodopsin-2 using the synapsin promoter; Puro-CAG-ASAP1 expression is driven by the chicken beta-actin promoter; and GCaMP6s expression is driven by the cytomegalovirus promoter in mammalian cells.

General Imaging Parameters

Epifluorescence imaging was performed on an AxioExaminer Z-1 (Zeiss) equipped with a Spectra-X Light engine LED light (Lumencor), controlled with Slidebook (v6, Intelligent Imaging Innovations). Co-incident excitation with multiple LEDs was controlled by Lumencor software triggered through a Digidata 1332A digitizer and pCLAMP 10 software (Molecular Devices). Images were acquired with either a W-Plan-Apo 20×/1.0 water objective (20×; Zeiss) or a W-Plan-Apo 63×/1.0 water objective (63×: Zeiss). Images were focused onto either an OrcaFlash4.0 sCMOS camera (sCMOS; Hamamatsu) or an eVolve 128 EMCCD camera (EMCCD; Photometrix).

Multicolor Imaging of BeRST 1 in HEK Cells and Photostability

HEK cells were incubated with a HBSS solution (Gibco) containing BeRST 1 (1.0 µM), Hoechst 33342 (1.0 µM, Molecular Probes) and Rhodamine 123 (5.0 µM, Sigma-Aldrich) at 37° C. for 15 min. Microscopic images were acquired with a W-Plan-Apo 63×/1.0 objective (Zeiss) and OracFlash4.0 sCMOS camera (Hamamatsu). For BeRST 1 images, the excitation light was delivered from a LED (67 $W/cm^2$; 100 ms exposure time) at 631/28 (bandpass) nm and emission was collected with a quadruple emission filter (430/32, 508/14, 586/30, 708/98 nm) after passing through a quadruple dichroic mirror (432/38, 509/22, 586/40, 654 nm LP). For Hoechst 33342 images, the excitation light was delivered from a LED (33 $W/cm^2$; 100 ms exposure time) at 390/22 nm and emission was collected with an emission filter (540/50 nm) after passing through a dichroic mirror (510 nm LP). For Rhodamine 123 images, the excitation light was delivered from a LED (57 $W/cm^2$; 100 ms exposure time) at 475/34 nm and emission was collected with an emission filter (540/50 nm) after passing through a dichroic mirror (510 nm LP).

HEK cells were incubated separately with BeRST 1 (0.20 µM) and VF2.1.Cl (0.20 µM) in HBSS at 37° C. for 15 min. Data were acquired with a W-Plan-Apo 63×/1.0 objective (Zeiss) and Evolve 128 emCCD camera (Photometrics). Images (pixel size 0.38 µm×0.38 µm) were taken every 20 sec for 10 min with constant illumination of LED (162 $W/cm^2$; 100 ms exposure time). For BeRST 1 images, the excitation light was delivered at 631/28 nm and emission was collected with a quadruple emission filter (430/32, 508/14, 586/30, 708/98 nm) after passing through a quadruple dichroic mirror (432/38, 509/22, 586/40, 654 nm LP). For VF2.1.Cl images, the excitation light was delivered at 475/34 nm and emission was collected with an emission filter (540/50 nm) after passing through a dichroic mirror (510 nm LP). The obtained fluorescence curves (background subtracted) were normalized with the fluorescence intensity at t=0 and averaged (six different cells of each dye).

Extracellular Stimulation Experiments

Extracellular field stimulation was delivered by Grass Stimulator connected to a recording chamber containing two platinum electrodes (Warner), with triggering provided through a Digidata 1332A digitizer and pCLAMP 10 software (Molecular Devices). Action potentials were triggered by 1 ms 80 V field potentials delivered at 5 Hz. To prevent recurrent activity the HBS bath solution was supplemented with synaptic blockers 10 µM 2,3-Dioxo-6-nitro-1,2,3, 4-tetrahydrobenzo[f]quinoxaline-7-sulfonamide (NBQX; Santa Cruz Biotechnology) and 25 µM DL-2-Amino-5-phosphonopentanoic acid (APV; Sigma-Aldrich). Functional imaging of BeRST 1 was performed using the EMCCD camera and a 63× objective. BeRST 1 was excited with a 631 nm light (LED; 631 nm, 28 nm bandpass) with an intensity of 127 $W/cm^2$. Emission from BeRST 1 was collected with a 680/10 nm bandpass emission filter (after passing through a quadruple dichroic mirror (432/38 nm, 509/22 nm, 586/40 nm, 654 nm LP) or for GCaMP6s and ASAP experiments a QUAD filter (quadruple emission filter (430/32 nm, 508/14 nm, 586/30 nm, 708/98 nm) after passing through the quadruple dichroic mirror. Optical sampling rate of BeRST 1 imaging was 0.5-0.53 kHz, except when imaging with ASAP1 (1.25 kHz). Green spectrum genetic tools (GFP, GCaMP6s and ASAP1) were illuminated using 475 nm light (LED; 475 nm, 34 nm bandpass). For functional imaging an intensity of 33 W/cm$^2$ for GCaMP6s and 200 W/cm$^2$ for the more weakly fluorescent ASAP1 was used, which is the maximum 475 nm LED intensity for the system. Emission was collected with a 540/50 nm bandpass filter after passing through a 510 nm longpass dichroic. Functional imaging of GCaMP6s and ASAP was performed at 40 Hz and 1.25 kHz, respectively. Images showing cellular morphology were performed by switching to a lower magnification 20× objective in conjunction with either the EMCCD (GCaMP6s/ASAP1) or sCMOS (GFP) camera.

Voltage Sensitivity in HEK Cells

Functional imaging of BeRST 1 was performed using a 20× objective paired with image capture from the EMCCD camera at a sampling rate of 0.5 kHz. BeRST 1 was excited using the 633 nm LED with an intensity of 6.7 W/cm$^2$. For initial voltage characterization (see, FIG. 4) emission was collection with the QUAD filter and dichroic (see above). For investigation into voltage sensitivity during excitation cross-talk (see, FIG. 11) BeRST 1 was excited by a 633 nm LED as above and 390 nm light (violet LED, 20 nm bandpass) with an intensity of 3.3 W/cm$^2$ and emission was collected with a 680/10 nm bandpass emission filter.

Imaging Groups of Cells

Imaging experiments looking a functional responses from many>5 neurons (see, FIG. 8 and FIG. 15) required a larger field of view which were obtained using the sCMOS camera with a 20× objective. BeRST 1 was excited using a 633 nm LED with an intensity of 20 W/cm$^2$ and emission was collected with a 680/10 nm bandpass emission filter. Images were binned 4×4 to allow sampling rates of 0.5 kHz. GFP was excited by the 475 nm LED and emission was collected with a 540/50 nm bandpass filter after passing through a 510 nm longpass dichroic. ChR2 positive neurons were identified by the YFP fusion by excitation with 510 nm light (LED; 510 nm, 25 nm bandpass) and emission was collected via a triple emission filter (473/22 nm, 543/19 nm, 648/98 nm) after passing through a triple dichroic mirror (475/30 nm, 540/25 nm, 642/96 nm. ChR2 was activated by 80 mW/cm$^2$, 5 ms pulses of 475 nm LED light at a frequency of 5 Hz.

Imaging of BeRST 1 in Patch-Clamped Hippocampal Neurons

Functional imaging of patched neurons was performed using an EMCCD camera and a 20× objective. This objective has a larger working distance and allowed for positioning of the patch electrode. BeRST 1 was excited using a 633 nm LED with an intensity of 10 W/cm$^2$ and emission was collected with a 680/10 nm bandpass emission filter. For optical assessment of the action potential waveform (see, FIG. 5) the sampling rate was increased to 1.8 kHz. For all optical electrophysiology (see, FIG. 13 and FIG. 14) sampling rate was increased to 1 kHz. YFP images were collected as above. ChR2 was stimulated by 80m W/cm$^2$, 5 ms pulses of 475 nm LED light at a frequency of 5 Hz.

Cross-Excitation

Cross-talk was assessed by exciting hippocampal neurons loaded with (1 μM) BeRST 1 with 390 nm, 475 nm and 633 nm LEDs all illuminating with an intensity of 9.7 W/cm$^2$. Emission was collected with a 680/10 nm bandpass emission filter.

Image Analysis

Analysis of voltage sensitivity in HEK cells was performed using custom Matlab routines. Briefly, a region of interest (ROI) was selected automatically based on fluorescence intensity and applied as a mask to all image frames. Fluorescence intensity values were calculated at known baseline and voltage step epochs. For analysis of BeRST 1 voltage responses in neurons, regions of interest encompassing cell bodies were drawn in ImageJ and the mean fluorescence intensity for each frame extracted. The photostability of BeRST 1 allowed for the calculation of ΔF/F values by subtracting a mean background value from all raw fluorescence frames, bypassing the noise amplification which arises from subtracting background for each frame. All example traces were not averaged. For comparisons of action potentials recorded electrophysiologically and optically, imaging traces were analyzed using spike detection algorithms in the Clampfit 10 software (Molecular Devices). For cross-excitation quantification images were background subtracted. ROIs were made by thresholding to the 25% of the maximum pixel intensity to remove non-stained areas. Mean intensity values for stained neurons were calculated.

Electrophysiology

For electrophysiological experiments, pipettes were pulled from borosilicate glass (Sutter Instruments, BF150-86-10), with a resistance of 5-8 MΩ, and were filled with an internal solution; (in mM) 115 potassium gluconate, 10 BAPTA tetrapotassium salt, 10 HEPES, 5 NaCl, 10 KCl, 2 ATP disodium salt, 0.3 GTP trisodium salt (pH 7.25, 275 mOsm). Recordings were obtained with an Axopatch 200B amplifier (Molecular Devices) at room temperature. The signals were digitized with Digidata 1332A, sampled at 50 kHz and recorded with pCLAMP 10 software (Molecular Devices) on a PC. Fast capacitance was compensated in the on-cell configuration. For all electrophysiology experiments, recordings were only pursued if series resistance in voltage clamp was less than 30 MΩ.

For whole-cell, voltage clamp recordings in HEK 293T cells were held at −60 mV and 100 ms hyper- and de-polarizing steps applied from −100 to +100 mV in 20 mV increments.

For whole-cell, current clamp recordings in hippocampal neurons, following membrane rupture, resting membrane potential was assessed and recorded at I=0 and monitored during the data acquisition. Neurons were switched to current clamp mode if they displayed series resistance in voltage clamp <30 MΩ. Pipette tip resistance was corrected by performing bridge balance compensation.

To test if loading of BeRST 1 onto the membrane of neurons has any effect on their action potential firing, ten 500 ms current steps were injected into neurons, in increments of 0.05 pA. The first action potential from each sweep was analyzed in Clampfit 10 software (Molecular Devices) to give amplitude and kinetic data. The cell capacitance determined by the Clampex software during recording. To evoke single action potentials for electrophysiological and imaging comparisons, short (10 ms) current injections were applied which were 2× the threshold required to evoke a single action potential. Analysis of action potentials was performed using spike detection algorithms in the Clampfit 10 software.

To record ChR2-evoked action potentials electrophysiologically, neurons were held in cell-attached mode (seals 0.5-1 G Ω) or following membrane rupture, data was acquired at I=0.

Design and Synthesis of Sulfonated Silicon Rhodamine

The development of Berkeley Red Sensor of Transmembrane potential 1 (BeRST 1, "burst"), a voltage-sensitive sulfonated silicon-rhodamine (Si-rhodamine) fluorophore is described. BeRST 1 features a Si-rhodamine core bearing a sulfonic acid on the meso aryl ring (termed Berkeley Red or "BR"). This sulfonated Si-rhodamine (see Scheme 1), provides NIR excitation and emission profiles on account of the Si-substituted xanthene, and improved retention of the dye at the extracellular surface of cell membranes, due to the anionic sulfonate (see below).

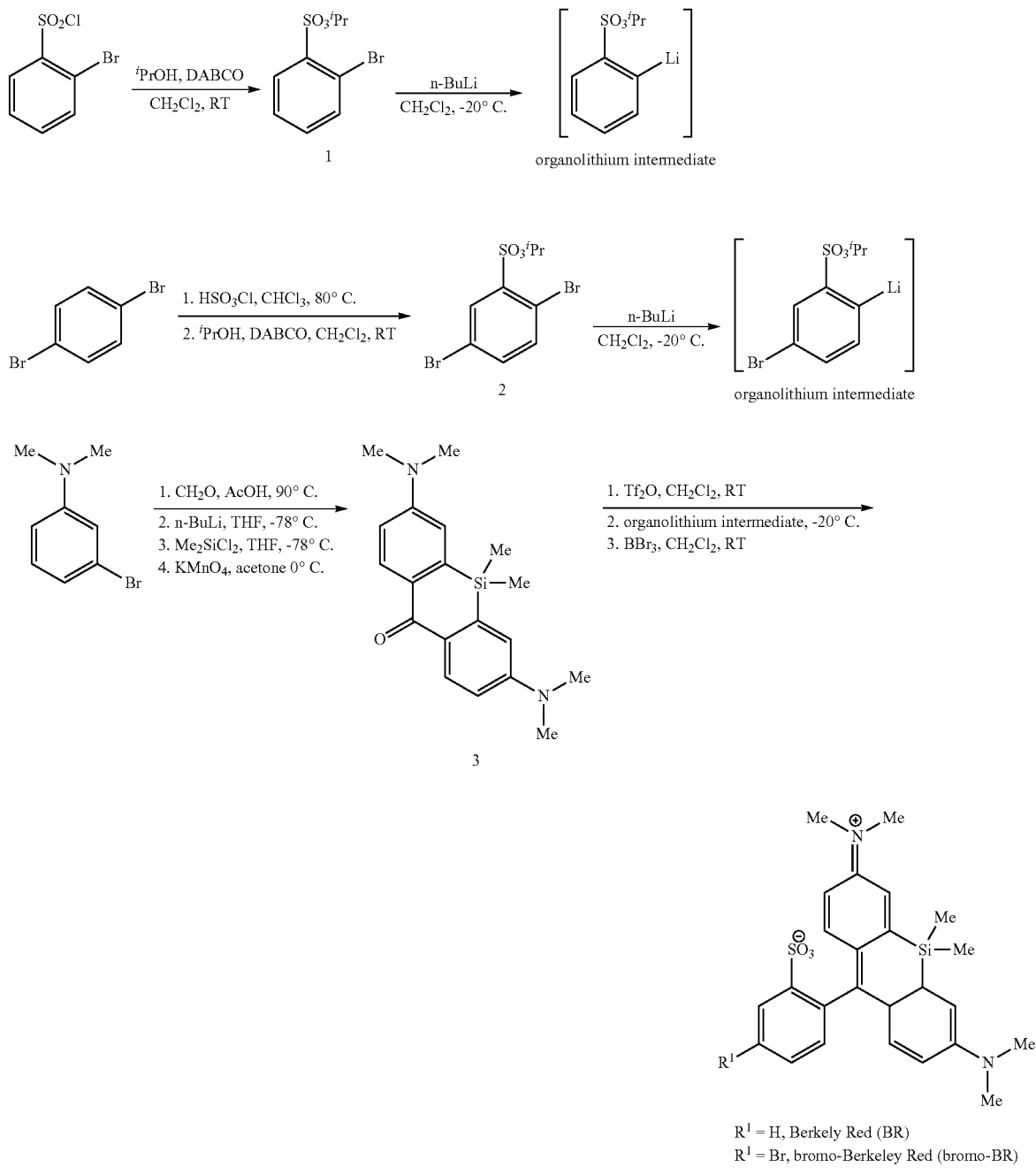

$R^1$ = H, Berkely Red (BR)
$R^1$ = Br, bromo-Berkeley Red (bromo-BR)

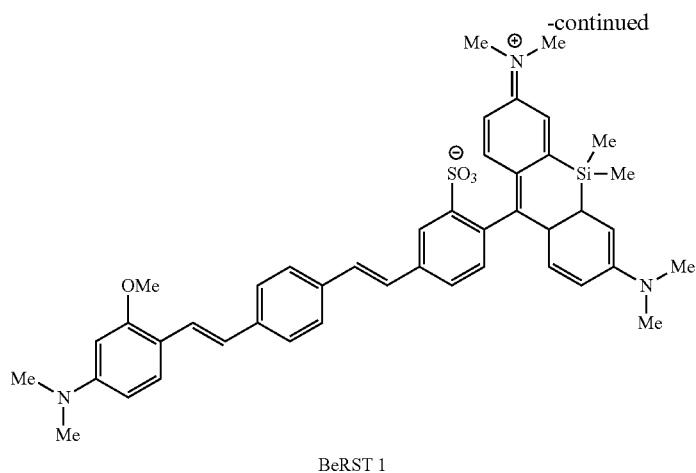

BeRST 1

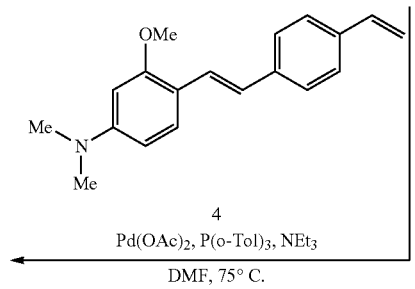

BR was synthesized in three steps from intermediates 1 and 3, which are available in 1 and 4 steps, respectively. The key step in the synthesis of BR core with attendant sulfonate is the nucleophilic addition of an organolithium intermediate, derived from lithium-halogen exchange on 1, to xanthone 3 that had been activated with triflic anhydride. Deprotection of the isopropyl ester with BBr$_3$ provided BR in 9%, over three steps (Scheme 1).

Isopropyl 2,5-dibromobenzenesulfonate (2): 1, 4-diazabicyclo[2.2.2]octane (0.81 g, 7.2 mmol, 1.2 equiv) was slowly added to 2,5-dibromobenzenesulfonyl chloride (2.0 g, 6.0 mmol, 1.0 equiv) in 3:2 CH$_2$Cl$_2$/$^i$PrOH (v/v) (5.0 mL) at 0° C. After a white precipitate started to form, the reaction mixture was warmed to ambient temperature and stirred for 30 min. After removing the precipitate by filtration, the filtrate was concentrated in vacuo and purified by flash column chromatography (5:1 hexanes/EtOAc) to afford the product as a white solid (1.3 g, 3.7 mmol, 62%). $^1$H NMR (400 MHz, CDCl$_3$) δ8.25 (d, J=2.3 Hz, 1H), 7.63 (d, J=8.4 Hz, 1H), 7.57 (dd, J=8.4, 2.3 Hz, 1H), 4.86 (sep, J=6.3 Hz, 1H), 1.38 (d, J=6.3, 6H); $^{13}$C NMR (150 MHz, CDCl$_3$) δ138.8, 137.2, 136.8, 134.3, 121.4, 119.5, 79.3, 22.8; HRMS (EI) calc'd for C$_9$H$_{10}$Br$_2$O$_3$S$^+$[M]$^+$355.8712, found, 355.8717.

5-Bromo-2-(7-(dimethylamino)-3-(dimethyliminio)-5,5-dimethyl-3, 5-dihydrodibenzo[b,e]silin-10-yl) benzenesulfonate (i.e., bromo-Berkeley Red): trifluoromethanesulfonic anhydride (0.10 mL, 0.59 mmol, 1.9 equiv) was added to a solution of 3 (0.10 g, 0.31 mmol, 1.0 equiv) in CH$_2$Cl$_2$ (1.0 mL). The solution was then stirred at ambient temperature for 30 min (Solution A). In another flask, 2 (0.33 g, 0.93 mmol, 3.0 equiv) was dissolved in CH$_2$Cl$_2$ (2.0 mL). After cooling the solution to −20° C., n-BuLi (1.6 M in hexane, 0.58 mL, 0.93 mmol, 3.0 equiv) was slowly added. After 10 min, Solution A was added to the reaction mixture. The mixture was then stirred for 1 h. The crude isopropyl ester protected-product was obtained by PTLC (5:1:1 hexanes/EtOAc/CH$_2$Cl$_2$) and subjected to 1.0 M BBr$_3$ in CH$_2$Cl$_2$ (2.0 mL). The reaction mixture was stirred at ambient temperature overnight and purified by PTLC (10:1 CH$_2$Cl$_2$/CH$_3$OH) to afford the desired product as a dark blue solid (25 mg, 0.046 mmol, 15%). $^1$H NMR (600 MHz, CDCl$_3$) δ8.51 (d, J=2.0 Hz, 1H), 7.53 (dd, J=8.1, 2.0 Hz, 1H), 7.32 (d, J=9.5 Hz, 2H), 6.99 (d, J=2.8 Hz, 2H), 6.89 (d, J=8.1 Hz, 1H), 6.58 (dd, J=9.5, 2.8 Hz, 2H), 3.25 (s, 12H), 0.55 (apperent s, 3H), 0.53 (apparent s, 3H); $^{13}$C NMR (225 MHz, CDCl$_3$) δ173.6, 153.9, 148.3, 148.2, 143.5, 134.3, 132.2, 131.1, 130.2, 129.0, 122.9, 119.4, 113.3, 40.6, −0.9, −1.2; HRMS (ESI) calcd for C$_{25}$H$_{27}$BrN$_2$NaO$_3$SSi$^+$[M+Na]$^+$565.0587, found, 565.0590.

(2-(7-(Dimethylamino)-3-(dimethyliminio)-5,5-dimethyl-3, 5-dihydrodibenzo[b,e]silin-10-yl) benzenesulfonate) (i.e., Berkeley Red): was prepared according to the same procedure described above from 3 (50 mg, 0.15 mmol, 1.0 equiv), trifluoromethanesulfonic anhydride (26 μL, 0.15 mmol, 1.0 equiv), 1 (83 mg, 0.30 mmol, 1.5 equiv) and n-BuLi (1.6 M in hexane, 0.19 mL, 0.30 mmol, 1.5 equiv). The product was obtained as a dark blue solid (6.3 mg, 0.014 mmol, 9%). $^1$H NMR (600 MHz, CDCl$_3$) δ8.35 (dd, J=8.4, 1.3 Hz, 1H), 7.54 (ddd, J=8.4, 7.5, 1.3 Hz, 1H), 7.39 (apparent td, J=7.5, 1.3 Hz, 1H), 7.36 (d, J=9.6 Hz, 2H), 6.99 (dd, J=7.5, 1.3 Hz, 1H), 6.98 (d, J=2.9 Hz, 2H), 6.56 (dd, J=9.6, 2.9 Hz, 2H), 3.23 (s, 12H), 0.56 (apparent s, 3H), 0.53 (apparent s, 3H); $^{13}$C NMR (150 MHz, CDCl$_3$) δ175.8, 153.9, 148.2, 146.8, 143.8, 135.3, 129.4, 129.4, 128.9, 128.6, 127.9, 119.2, 113.3, 40.5, −0.9, −1.2; HRMS (ESI) calcd for C$_{25}$H$_{28}$N$_2$NaO$_3$SSi$^+$[M+Na]$^+$487.1482, found, 487.1478.

Figure 2B:
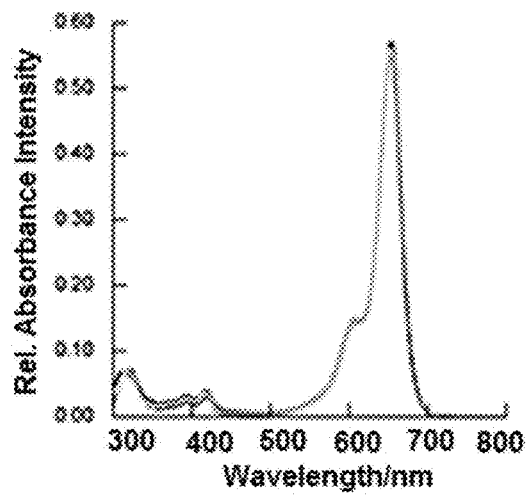
Figure 2C:
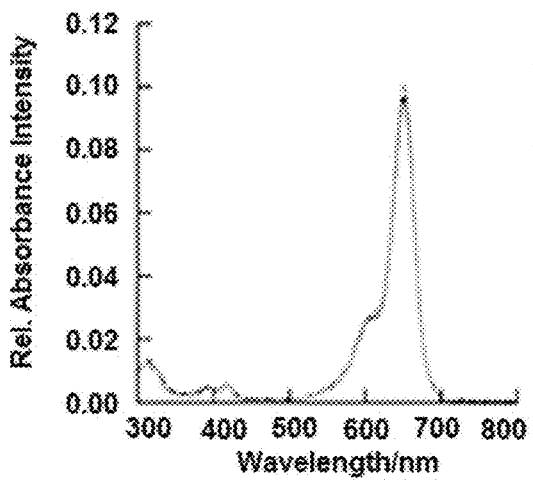
Figure 2D:
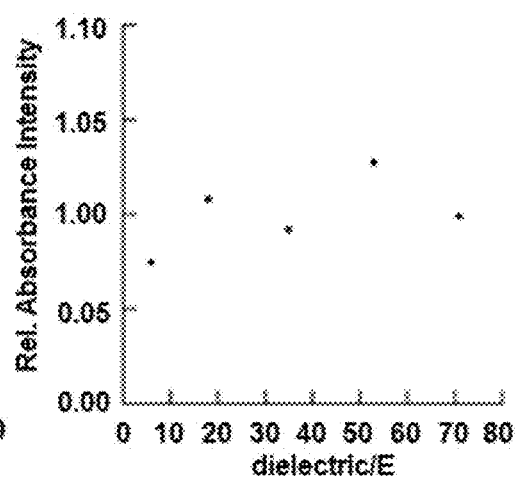
Figure 2E:
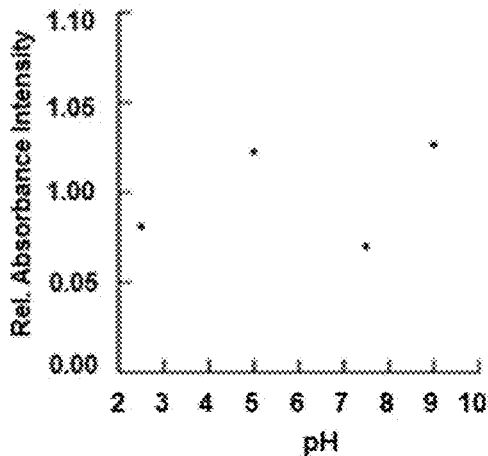

Berkeley Red (BR) displays an absorbance profile centered at 658 nm and an extinction coefficient of 150,000 M$^{-1}$ cm$^{-1}$ in aqueous buffer (FIG. 1A, 50 mM TBS, pH 7.5, 0.1% SDS). BR features NIR fluorescence, emitting strongly at 681 nm ($\Phi_{fl}$=0.24 in TBS/SDS buffer and 0.32 in methanol). A key requirement for the use of BR in voltage sensing applications is that BR not cyclize to the non-fluorescent state in low dielectic environments like cell membranes. Although this spirocyclization is a useful property for super-resolution microscopy, cyclization leads to a more hydrophobic conformation and encourages the passage of the voltage sensor through the plasma membrane. Staining of internal membranes and cytosol then sharply increases background fluorescence and limits the useful signal one can extract from an imaging experiment. As predicted, placement of a sulfonate group on the meso aryl ring prevented spirocyclization, with no change in absorbance observed in either acidic or basic environments (pH 2.5 to 9) (see, FIG. 2C and E). BR absorbance remains unchanged (see, FIG. 2B and D) through a range of solvent dielectric constants from ε=6 (10% water/dioxane v/v) to ε=71 (90% water/dioxane v/v), confirming that BR displays minimal solvatochromism. The environmental insensitivity of BR stands in stark contrast to carboxy Si-Rhodamine derivatives, which display massive absorbance fluctuations upon changes in the dielectric constant of the solvent. The spirocyclization is effectively minimized by replacement of carboxyl with sulfonate. It was further confirmed that BR's sulfonic acid renders it cell-impermeant, as HEK cells bathed in BR showed negligible cytosolic fluorescence (see, FIG. 3).

Design and Synthesis of BeRST 1

Having established that sulfonated Si-rhodamine BR possesses bright, NIR fluorescence and absorbance that does not vary with pH or solvent dielectric, BR was functionalized with a phenylenevinylene molecular wire to generate BeRST 1. The key brominated Berkeley Red (bromo-BR, Scheme 1) was synthesized in 15% yield via chelation-assisted lithiation of 2. Lithiation was accomplished in $CH_2Cl_2$ at −20° C., with triflic anhydride used to activate 3 for addition of the organolithium species. A variety of other conditions involving different combinations of solvents (THF, $CH_2Cl_2$), reagents (nBuLi, iPrMgCl·LiCl), additives ($MgSO_4$), and temperatures (−78° C., −40° C. and 22° C.) all gave no reaction, insufficient yield, or complicated mixtures.

Regio-selective lithiation under the optimized reaction conditions was confirmed by quenching the generated lithium species with acid to give a product consistent by $^1H$ NMR with ortho-lithiation (see, FIG. 26). Pd-catalyzed Heck coupling of bromo-BR with methoxy-substituted phenylenevinylene dimethyl aniline molecular wire 4 was available in 3 steps and provided BeRST 1 in 62% yield after purification on silica gel. BeRST 1 exhibits spectral properties similar to the parent BR dye, with excitation and emission centered at 658 nm and 683 nm (compare FIG. 1A to FIG. 2A). Compared to BR, the quantum yield of BeRST 1 is substantially reduced, at 0.017 and 0.022 in aqueous buffer and MeOH, respectively.

(5-((E)-4-((E)-4-(Dimethylamino)-2-methoxystyryl) styryl)-2-(7-(dimethylamino)-3-(dimethyliminio)-5, 5-dimethyl-3,5-dihydrodibenzo[b,e]silin-10-yl)benzenesulfonate) (BeRST 1). Bromo-Berkeley Red (5.0 mg, 9.2 µmol, 1.0 equiv), 4 (2.6 mg, 9.3 µmol, 1.0 equiv), $Pd(OAc)_2$ (1.1 mg, 4.5 µmol, 0.50 equiv), P(o-tol)$_3$ (2.8 mg, 9.2 µmol, 1.0 equiv) and $NEt_3$ (50 µL) were dissolved in DMF (0.10 mL). The solution was stirred at 75° C. and the progress of the reaction was monitored by TLC. After the reaction was complete, the crude mixture was purified by PTLC (10:1 $CH_2Cl_2/CH_3OH$) to afford the product as a dark green solid (4.2 mg, 5.7 µmol, 62%). $^1H$ NMR (900 MHz, 10:1 $CDCl_3/CD_3OD$ (v/v)) δ8.34 (d, J=1.8 Hz, 1H), 7.53 (dd, J=7.8, 1.8 Hz, 1H), 7.46 (apparent s, 4H), 7.43 (d, J=8.5 Hz, 1H), 7.39 (d, J=16.4 Hz, 1H), 7.27-7.21 (m, 3H), 7.14 (d, J=16.4 Hz, 1H), 6.99-6.94 (m, 3H), 6.91 (d, J=16.4 Hz, 1H), 6.55 (dd, J=9.7, 2.8 Hz, 2H), 6.31 (dd, J=8.5, 2.4 Hz, 1H), 6.19 (d, J=2.4 Hz, 1H), 3.85 (s, 3H), 3.21 (s, 12H), 2.95 (s, 6H), 0.50 (apparent s, 3H) 0.48 (apparent s, 3H); $^{13}C$ NMR (225 MHz, 10;1 $CDCl_3/CD_3OD$ (v/v)) δ173.3, 158.0, 153.9, 151.4, 148.1, 145.2, 143.3, 138.7, 138.5, 134.9, 134.4, 130.4, 129.6, 128.8, 127.1, 126.9, 126.2, 126.2, 126.2, 125.9, 124.1, 123.7, 119.3, 115.0, 113.2, 105.2, 95.6, 55.3, 40.3, −1.2, −1.4; HRMS (ESI) calcd for $C_{44}H_{48}N_3O_4SSi^+[M+H]^+$ 742.3129, found, 742.3118.

Cellular Characterization of BeRST 1

BeRST 1 localizes to cell membranes when bath applied to HEK cells (see, FIG. 1C). Importantly, BeRST 1 fluorescence remained localized to the cell membrane throughout the course of imaging experiments. This is in contrast to the BR fluorophore in isolation, which displays negligible cellular fluorescence after loading under identical conditions-further establishing the ability of the sulfonate in BeRST 1 and BR to prevent dye internalization (see, FIG. 3A vs. 3C).

BeRST 1 shows excellent photostability (see, FIG. 1B), with a bleaching half-life of approximately 5 minutes under intense illumination conditions (I=162 W/cm$^2$, 631 nm LED). Which is approximately an order of magnitude higher than intensities used for BeRST 1 imaging in concert with other optical tools (see, FIGS. 8, 13 and 15). By comparison, VF2.1.Cl, which has a similar voltage sensitivity, 27% ΔF/F per 100 mV, has a bleaching half-life of <60 seconds under identical illumination intensities (I=162 W/cm$^2$, 475 nm LED). Since BeRST 1 has a larger extinction coefficient than VF2.1.Cl at the incident irradiation (150,000 vs 90,000), this comparison slightly underestimates the photostability of BeRST 1 (Si-rhodamine) relative to VF2.1.Cl (fluorescein). To determine the voltage sensitivity of BeRST 1, whole-cell patch clamp electrophysiology was performed on HEK cells loaded with 1 µM BeRST 1 (see, FIG. 4A and 4B). Depolarization of voltage-clamped HEK cells with BeRST 1 results in prompt increases in fluorescence, while hyperpolarization gives fluorescence decreases (see, FIG. 4B). BeRST 1 has a voltage sensitivity of approximately 24%±5% ΔF/F per 100 mV—comparable to first generation blue light-excitable VoltageFluors—and is linear over a physiologically relevant range spanning ±100 mV (see, FIG. 4B).

Voltage Imaging with BeRST 1 in Neurons

BeRST 1 stained cell membranes of cultured hippocampal neurons equally well (see, FIG. 5A and 5B). Whole-cell patch-clamp electrophysiology on cultured neurons loaded with BeRST 1 established that BeRST 1 can detect action potentials (APs) in single trials. Action potentials were evoked under current clamp mode, and the resulting optical response matched the recorded $V_{mem}$ changes exactly (see, FIG. 5D). Optically recorded action potentials (1.8 kHz optical sampling) were indistinguishable from a simultaneously recorded traditional electrophysiological trace. When measured electro-physiologically, the FWHM duration of action potentials were 1.65±0.15 ms, while optical action potential records gave values of 1.97±0.14 ms (n=7 cells each condition). The difference of 0.32 ms is far less than the optical sampling interval of 0.56 ms, and therefore within the error of measurement for the imaging apparatus. Optical responses from BeRST 1 for action potentials under these conditions were approximately 9.5% ΔF/F (±1.2%, n=7 cells).

Using whole-cell patch clamp electrophysiology without imaging, it was established that the presence of BeRST 1 has no discernable effect on the ability of neurons to fire action potentials or on the measured properties of the action potentials. No difference was found in peak action potential amplitude, duration, rise time, decay time or cellular capacitance when comparing the electrophysiological response to stimulation in neurons with or without 1 µM BeRST 1 (n=12 and 11 dye-free and dye-loaded neurons, see FIG. 6). Action potentials were readily detectable under field stimulation conditions as well, giving 17.8% ΔF/F (±1.6%, n=5 cells) (see, FIG. 5C). In most cases, a repolarization is visible following the action potential, further highlighting the utility of BeRST 1 to detect and report on full action potential waveforms.

Multi-Color Imaging with BeRST 1

One of the benefits of voltage sensors in the NIR window is that these new tools can be interfaced with a wide variety of blue, green, and red optical tools. Of particular interest are the genetically encoded optical tools based on GFP, since on the whole, these fluorescent proteins are more widely used and exhibit more predictable cellular and photophysical behavior than their red fluorescent counterparts. It was first established that BeRST 1 can perform multi-color imaging with some commonly used molecular probes for cellular organelles: the nucleus and mitochondria. Simultaneous three-color live cell imaging was performed with BeRST 1 (see, FIG. 1C), rhodamine 123 mitochondrial stain (see, FIG. 1D) and Hoescht 33342 nuclear stain (see, FIG. 1E). Under these conditions distinct cellular components were clearly visible in 3 colors, establishing the utility of BeRST 1 for multicolor imaging. (see, FIG. 1C-F)

Functional information is often required from a sub-set of cells, which are typically identified by the targeted expression of a fluorescent protein. Whether BeRST 1 could provide multi-color functional imaging, by pairing BeRST 1 staining with GFP labeling, was determined next. Neurons expressing cytosolic GFP were loaded with BeRST 1 and then action potentials were evoked via field stimulation (see, FIG. 7). Under these conditions, BeRST 1 gave large changes in fluorescence in cells not expressing GFP, approximately 9.2% ΔF/F per action potential (±1.6%), with a SNR of 62:1. GFP-expressing cells in the same field of view gave virtually identical responses (8.7±0.8% ΔF/F, SNR=63:1, n=5 pairs of cells) establishing that the response of BeRST 1 is not diminished by the presence of GFP, nor by optical bleedthrough or cross-excitation of GFP (see, FIG. 7). This methodology could therefore be used to label cells or subcellular locales of interest with an optically orthogonal fluorescent protein (GFP) and then record from regions of interest (ROIs) defined by the fluorescent protein. Although extracellular field stimulation confirmed that the presence of GFP does not attenuate the BeRST 1 optical response, it did not allow for the interrogation of independent signals coming from GFP-positive and -negative cells, since all neurons respond to extracellular field stimulation.

Figure 8A:
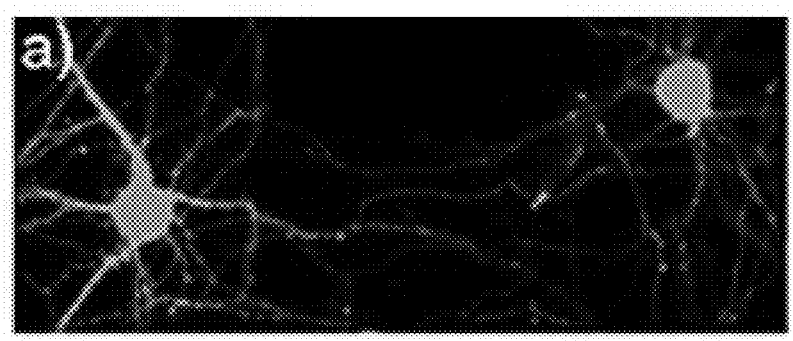
FIG. 8A-C presents spontaneous voltage imaging in GFP-labeled cells with BeRST 1. Epifluorescence images of rat hippocampal neurons expressing (A) GFP and (B) stained with BeRST 1. Scale bar is 20 µm. (C) Optical traces of spontaneous activity in neurons from panels (A) and (B). Numbers next to traces correspond to indicated cells in panel (B). Optical sampling rate is 500 Hz. Traces were background offset and bleaching was corrected in Clampfit.
Figure 8B:
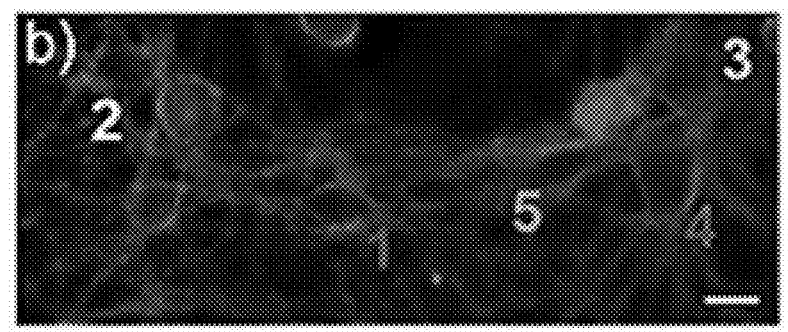
Figure 8C:
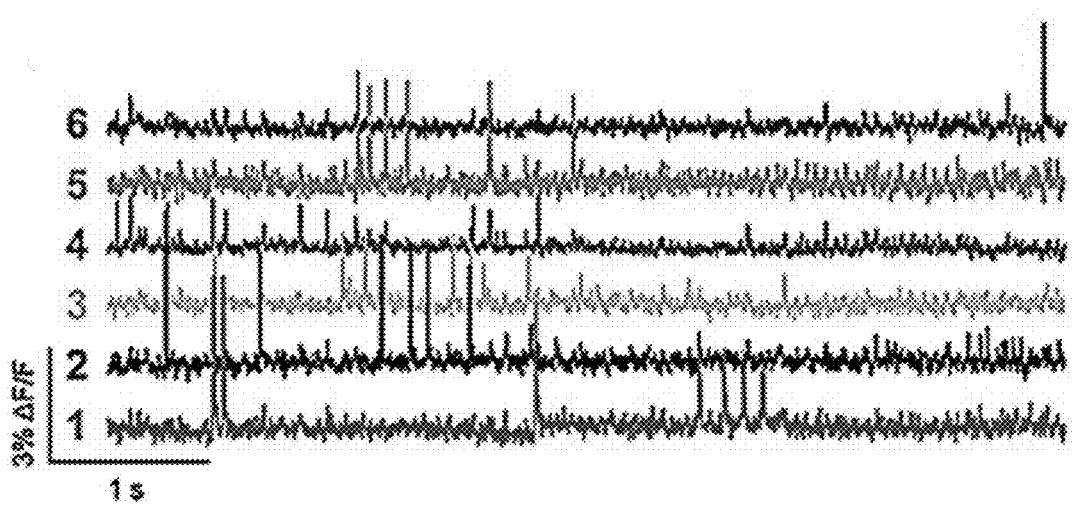

To demonstrate that individual neuronal activity could be spatially segregated in cultures expressing GFP, the spontaneous activity was imaged in the same cultures expressing GFP and labeled with BeRST 1. Using GFP to define regions of interest, the activity of the cell of interest could clearly be distinguished from the surrounding cells. In FIG. 8, the ROIs defined by the GFP-positive neurons (#3 and #6) clearly display activity strikingly different from the other four cells in the field of view. Taken together, these experiments demonstrate the ability of BeRST 1 to provide multisite optical recording of neuronal activity in parallel with a GFP counterstain.

The ability of BeRST 1 to participate in two-color, multi-functional imaging, that is, combining voltage imaging with either Ca2+ imaging, voltage imaging, or optogenetic manipulation via ChR2 was then determined. The GCaMP family of $Ca^{2+}$ sensors are one of the most widely used functional probes for systems and cellular neuroscience. However, because the excitation and emission spectrum of GCaMP lies squarely within the regime of previous generations of VoltageFluors (as well as other functional probes), this has precluded the use of GCaMPs with PeT-based voltage sensitive dyes. Neurons expressing the genetically encoded $Ca^{2+}$ sensor, GCaMP6s which provides large fluorescence increase in response to rising intracellular $Ca^{2+}$ concentration, were stained with BeRST 1 (see, FIG. 9A and 9B). GCaMP6s-positive neurons (see, FIG. 9B) displayed bright green cytosolic fluorescence, while membranes were clearly labeled with BeRST 1 (see, FIG. 9A). From a single cell expressing GCaMP6s and stained with BeRST 1, the action potentials via field stimulation were evoked, and optical recordings were obtained, first for the green channel for GCaMP6s and then in the NIR channel for BeRST 1 (see, FIG. 9A and B). In sequential optical traces, both the rise in $V_{mem}$ and rise in $[Ca^{2+}]_i$ are clearly visible (see, FIG. 9C). Dual BeRST 1 and GCaMP6s imaging enables discrimination of voltage and $Ca^{2+}$ transients, with the voltage transient (approximately 15% ΔF/F) preceding the measured GCaMP6s signal (approximately 5% ΔF/F) for a single evoked action potential (see, FIG. 9C). One of the advantages of voltage imaging is the ability to deconvolve fast spiking that $Ca^{2+}$ imaging, with its slower intrinsic signals and slow probe unbinding kinetics, often cannot resolve. When neurons expressing both GCaMP6s and stained with BeRST 1 were stimulated to evoke trains of action potentials at 5, 10, and 20 Hz, discrete $V_{mem}$ responses corresponding to individually evoked action potentials were visible in the BeRST 1 channel at all frequencies (see, FIG. 9D), while $Ca^{2+}$ response as measured by GCaMP6s were only discernable at 5 Hz, as measured by small changes in on the rising edge of GCaMP6s fluorescence (see, FIG. 9E). This highlights the ability of BeRST 1 to participate in functional imaging experiments in which multiple signals need to be interpreted in the same system.

The non-overlapping signals emanating from BeRST 1 and GFP-based fluorophores provide a unique opportunity to perform two-color voltage imaging. The genetically-encoded voltage sensor, ASAP1 was expressed in cultured neurons. As before, the neurons were stained with BeRST 1 (see, FIG. 10A-D). In response to an evoked train of action potentials (see, FIG. 10E), ASAP1 provided for decreases in relative fluorescence of about 6%±1.4% (S.E.M., with a signal to noise ratio, SNR, of 8:1, n=4 cells), which is consistent with the reported value of −4.8% ΔF/F. BeRST 1, in the same cell, under identical stimulation parameters (see, FIG. 10E), gives a 15%±2.1% increase (S.E.M., SNR of 41:1, n=4 cells), highlighting the utility of BeRST 1 for measurement of fast spiking events and for two-color voltage imaging with complementary genetically-encoded voltage sensors based on GFP.

Optical Electrophysiology with BeRST 1 and ChR2

BeRST 1 was interfaced with optogenetic tools like ChannelRhodopsin2 (ChR2) in order to demonstrate the feasibility of using light to both actuate and record the $V_{mem}$ of living cells in an "all-optical" electrophysiology methodology. The action spectrum of ChR2 (470 nm peak response), one of the more heavily-used optogenetic tools, contains significant overlap with the first generation of VoltageFluor dyes. Although red-shifted variants of ChR have been reported, all of them contain significant response peaks in the blue region of the spectrum. For this reason, it is advantageous to move the voltage-imaging component into the NIR region of the spectrum to avoid cross-talk in the optical channels for activation and recording.

Figure 12A:
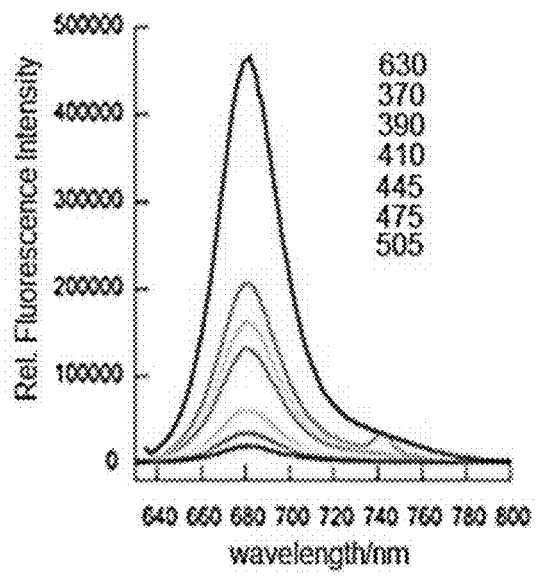
FIG. 12A-C provides for in vitro cross excitation of BeRST 1 and BR. Emission scans of (A) BeRST 1 and (B) BR in aqueous buffer (50 mM TBS, pH 7.5, 0.1% SDS) with differing excitation wavelengths. (C) Relative fluorescence emission intensity at 680 nm vs. excitation wavelength for BeRST 1 (black bars) and BR (grey bars).
Figure 12B:
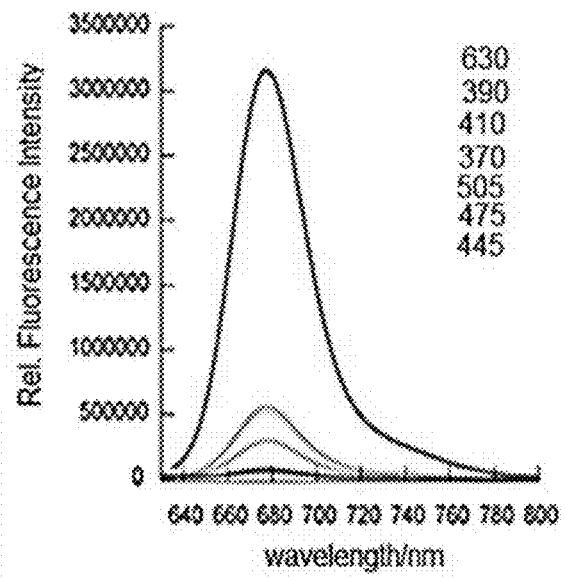
Figure 12C:
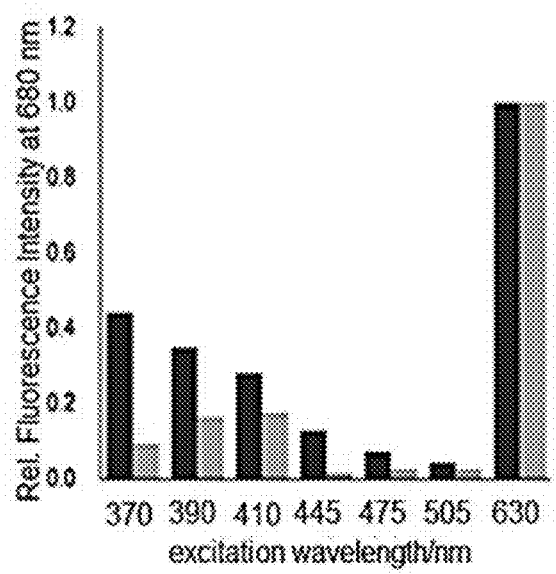
Figure 18:
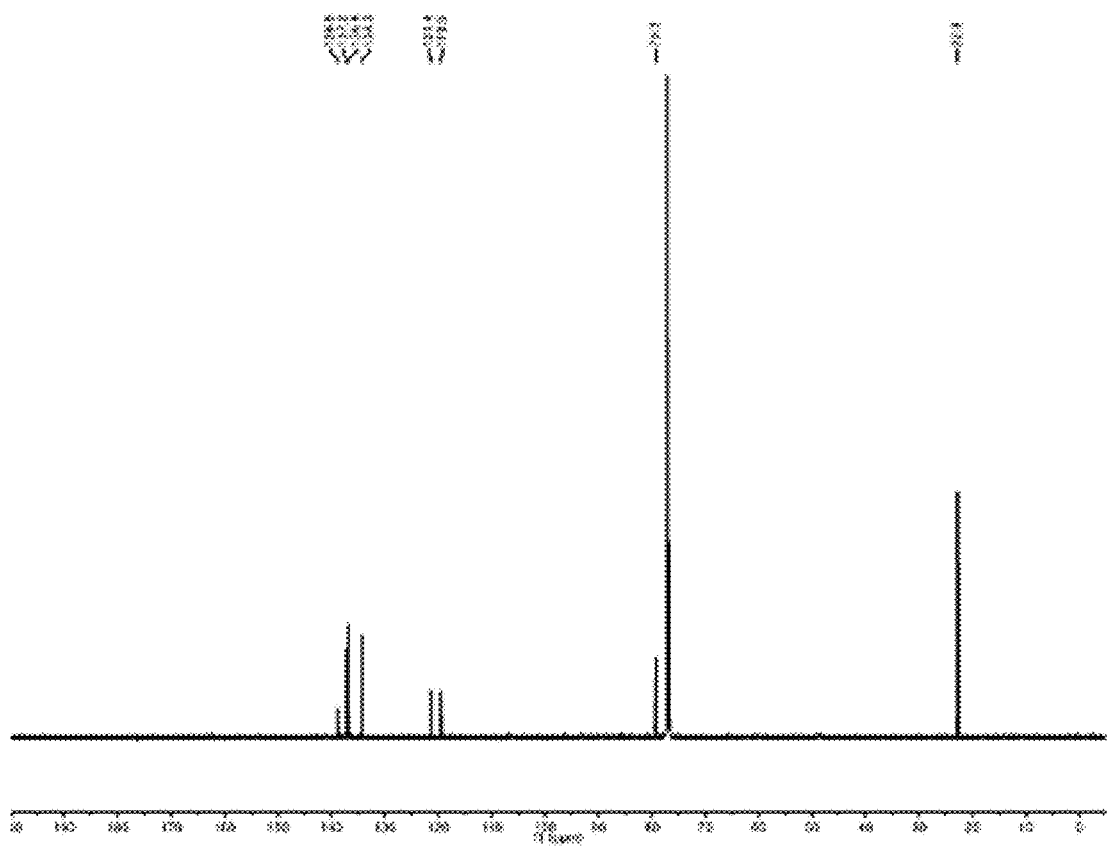
FIG. 18 shows the $^{13}C$ NMR of 2,5-dibromo-benzenesulfonic acid isopropyl ester.
Figure 19:
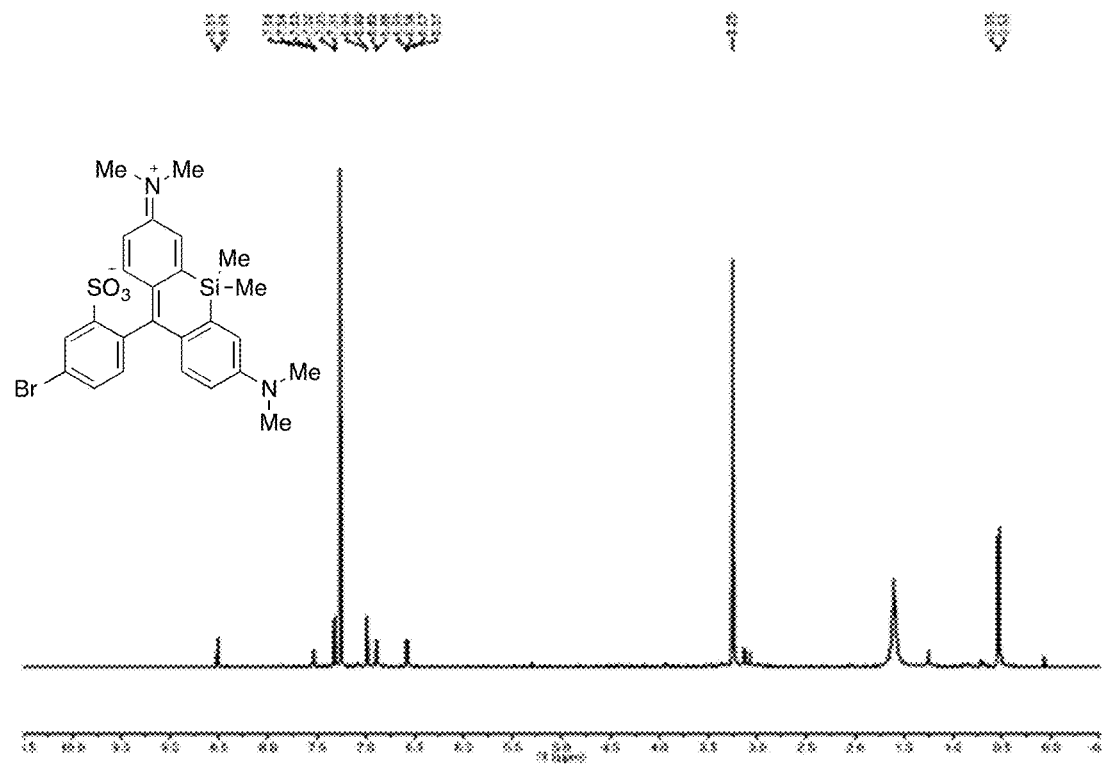
FIG. 19 shows the $^1H$ NMR of bromo-BR.
Figure 20:
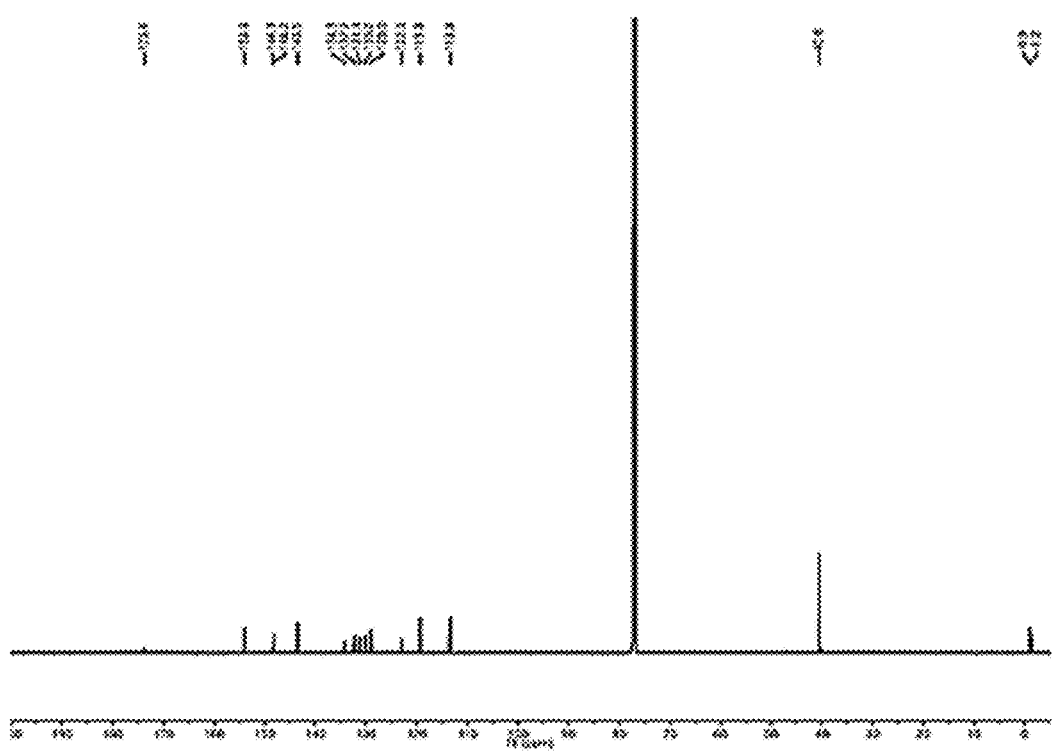
FIG. 20 shows the $^{13}C$ NMR of bromo-BR.
Figure 21:
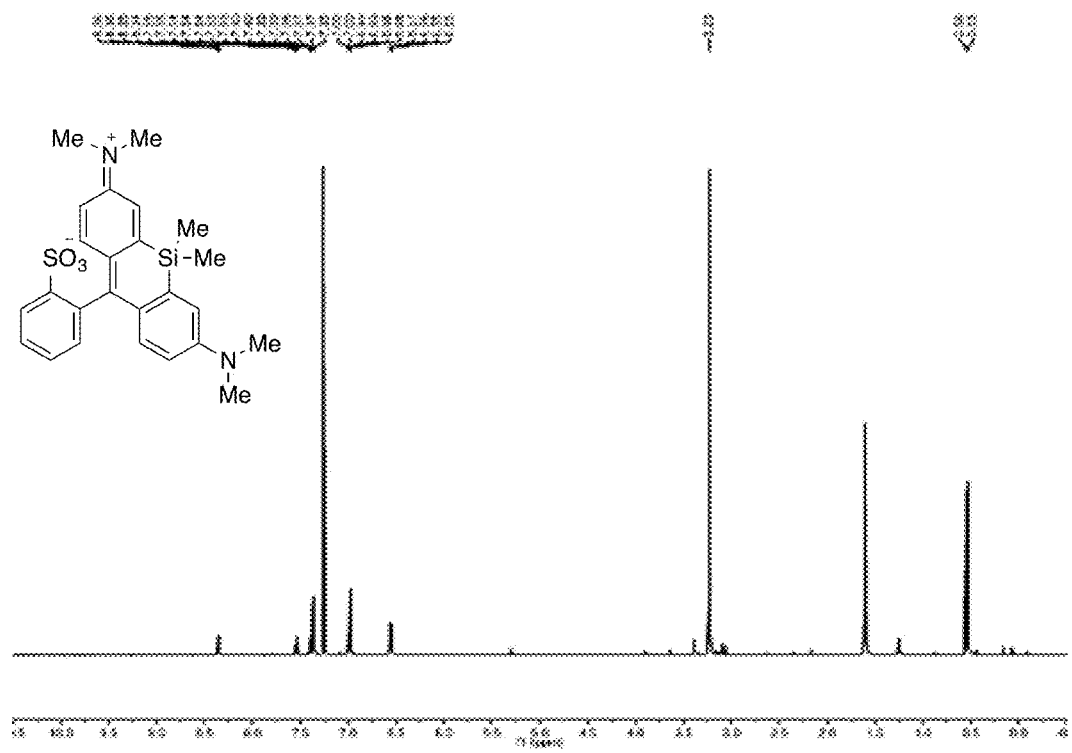
FIG. 21 shows the $^1H$ NMR of BR.
Figure 22:
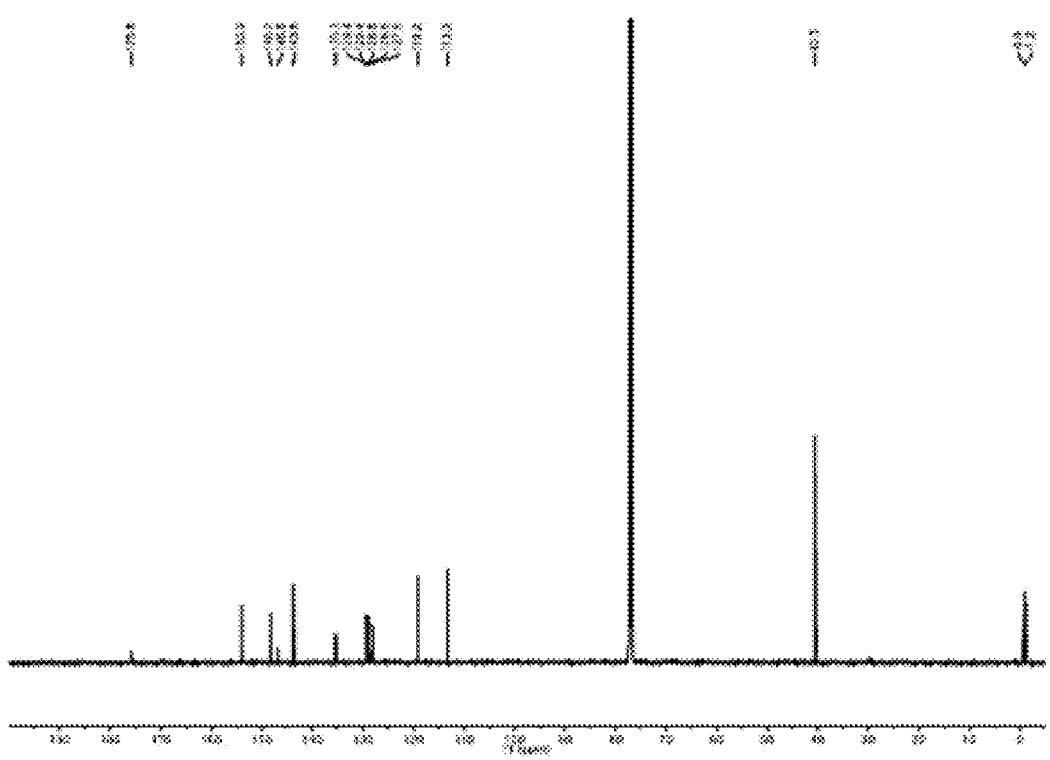
FIG. 22 shows the $^{13}C$ NMR of BR.
Figure 23:
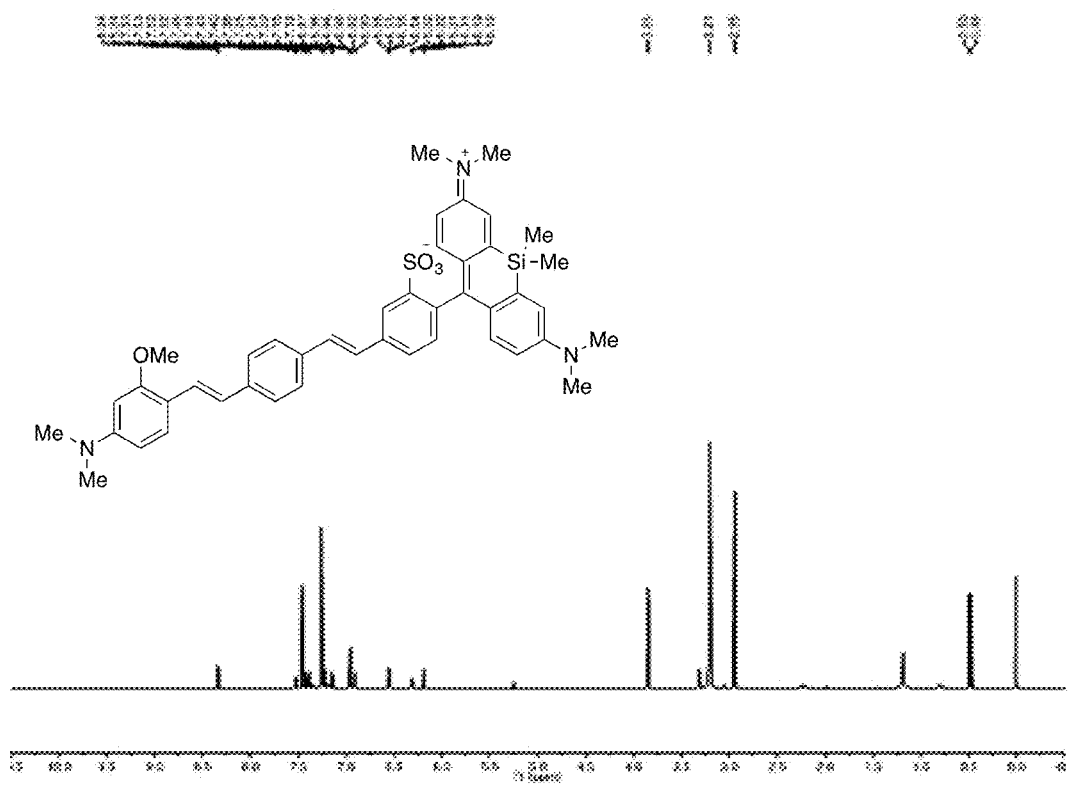
FIG. 23 shows the $^1H$ NMR of BeRST 1.
Figure 24:
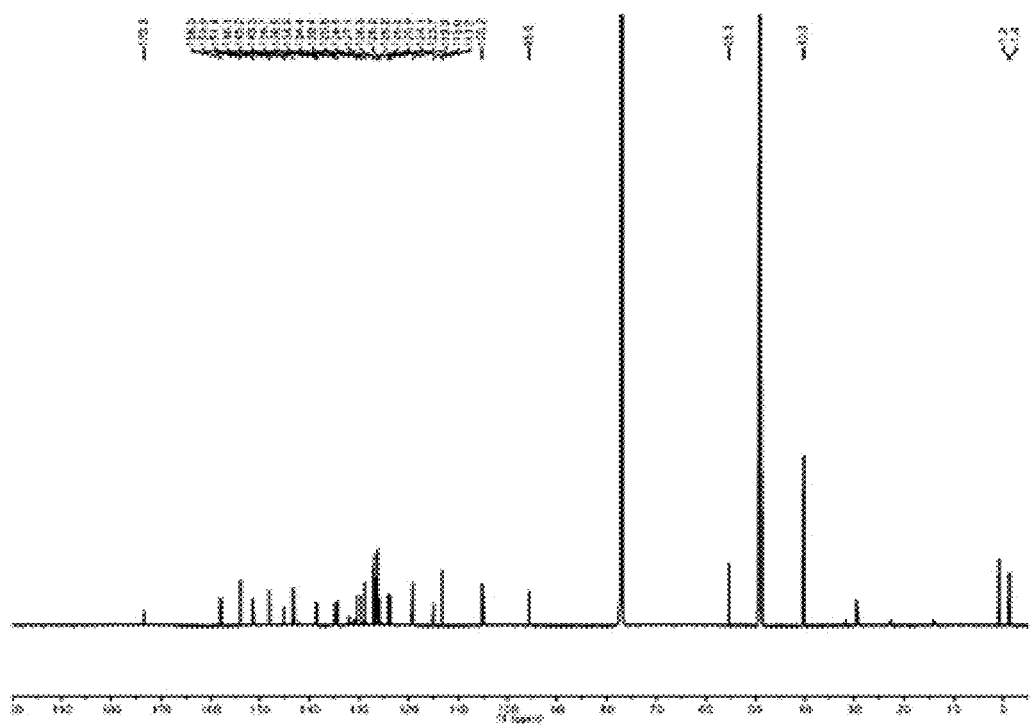
FIG. 24 shows the $^{13}C$ NMR of BeRST 1.

Before carrying out optical recording of light-induced action potentials, it was investigated whether any optical cross-talk exists between BeRST 1 and ChR2. A small amount of cross excitation was found for BeRST 1. When excited at 475 nm, BeRST 1-stained cells show fluorescence that is approximately 4% the intensity achieved with excitation at 631 nm (9.7 W/cm², 475 nm and 631 nm, see FIG. 11A-D). Because ChR2 requires much lower light intensity relative to typical imaging light intensities for BeRST 1 (80 mW/cm², 475 nm vs 20 W/cm², 631 nm for multicellular imaging), it was estimated that less than 0.1% of BeRST 1 signal comes from cross excitation of ChR2 in actual imaging experiments. Cross excitation is also observed upon excitation of BR and BeRST 1 derivatives in vitro (see, FIG. 12A and 12B). Excitation of BR or BeRST 1 derivatives in aqueous buffer with cyan light (475 nm) gives approximately 1% or 7% of the total emission when compared to excitation at 630 nm, respectively (see, FIG. 12C). Violet excitation (390 nm) in vitro gives 16% (BR) and 35% (BeRST 1) of full emission (see, FIG. 12C), which is consistent with cross excitation of BeRST 1 in cellular membranes (approximately 47% with 9.7 W/cm2 390 nm excitation) (see, FIG. 11C and D). HEK cells stained with BeRST 1 are voltage sensitive when imaged under violet illumination (see, FIG. 11E, 390 nm excitation, 3.3 W/cm², 680 nm emission).

Having established that negligible cross excitation of BeRST 1 occurs (<0.1%) under experimental conditions, it was then established whether BeRST 1 and ChR2 could function as optically orthogonal tools for probing and perturbing neuronal activity. Neurons transiently expressing a YFP-ChR2 fusion (see FIG. 13A and FIG. 14B) and loaded with BeRST 1 gave bright membrane staining, as expected (see FIG. 13B and FIG. 14A). Stimulation of ChR2 with brief pulses of cyan light (5 ms, 475 nm, 80 mW/cm²) resulted in light-induced spikes in membrane potential, as measured via patch clamp electrophysiology in either whole cell (see FIG. 13C and D) or cell-attached (see FIG. 14D) configurations. Control experiments in cells lacking ChR2 show no spiking. Optical recording of light-induced spikes with BeRST 1 matched the electrophysiologically recorded activity (see, FIG. 13C vs. D and E vs. F; and FIG. 14D and E). Of note is the high SNR achieved by BeRST 1 during optical recordings. Although the SNR of BeRST 1 is low compared to the highly sensitive whole-cell patch clamp method (see, FIG. 13C-F), optical sensitivity of BeRST 1 compares favorably with records acquired by the less sensitive on-cell patch clamp technique (see, FIG. 14D and E).

As a final demonstration of the efficacy of using BeRST 1 in conjunction with optogenetic tools, network behavior in cultured hippocampal neurons was probed. Analysis of neuronal connectivity and function with cellular resolution in intact brains remains an outstanding challenge, making cultured hippocampal neurons an attractive model system for studying both connectivity and function. Indeed, experimental evidence shows that neurons in culture make specific synaptic connections, mirroring connectivity encountered in vivo.

A large area of hippocampal neurons (370×62 μm, 20× magnification) stained with BeRST 1 and containing just a single neuron expressing YFP-ChR2 was imaged (see, FIG. 15A-C and FIG. 16). Continuous optical recording over a period of several seconds demonstrated, as before (see, FIG. 8) that most neurons remain relatively silent during the recording epoch. Activation of the YFP-ChR2-expressing neuron with cyan light (475 nm, 80 mW/cm², 5 ms at 5 Hz, see FIG. 15E-G, cyan bars) resulted, as before (see, FIG. 13), in bursts of spikes from the ChR2(+) neuron (see, FIG. 15, blue trace) that exactly followed the optical stimulation pattern. Unlike previous experiments, in which the optical response of only the ChR(+) cell was captured (see, FIG. 13 and FIG. 14), the larger recording area, provided information on how activation of a single neuron affected the surrounding cells (see, FIG. 15).

During the first optical stimulation (see, FIG. 15E and F, cyan bars), Neuron 1 (see, FIG. 15C-E, black cell and trace)—the closest neighbor to YFP-ChR2-expressing Neuron 2 (see, FIG. 8C-E, blue cell and trace)—fires a single AP in response to the second AP in Neuron 2 (see, FIG. 15E, first red box and FIG. 15G, first region). Neurons 3 (see, FIG. 15C-E, purple cell and trace) and 5 (see, FIG. 15C-E, orange cell and trace) are only weakly coupled to Neuron 2's firing and appear to initiate their own doublet of spikes that propagate into Neuron 4 (see, FIG. 15C-E, green cell and trace) and interrupt the optically induced firing pattern of Neuron 2 (see, FIG. 15D and E, first red box). This spike doublet is separated by approximately 12 ms and would be difficult to resolve with slower $Ca^{2+}$ imaging.

During the second epoch of light stimulation, the response of Neuron 1 (see, FIG. 15D and 15F, black cell and trace) is suppressed, and no longer appears strongly coupled to cues from optically-controlled Neuron 2 (see, FIG. 15D and F, blue cell and trace). The response of Neurons 3 and 5 are more strongly correlated to the firing of Neuron 2 (see, FIG. 15F and G, first red box), while Neuron 4 (see, FIG. 15D and F, green cell and trace) remains silent with the exception of several spontaneous bursts prior to optical activation of Neuron 2. Even in this "simple" cultured hippocampal model, a high degree of interconnectedness exists, which would not be observable through methods like $Ca^{2+}$ imaging. Together, these experiments establish the ability of BeRST 1 to work in concert with classic optogenetic tools to optically interrogate the complexity of neuronal connectivity and function.

A number of embodiments have been described herein. Nevertheless, it will be understood that various modifications may be made without departing from the spirit and scope of this disclosure. Accordingly, other embodiments are within the scope of the following claims.

What is claimed is:

1. A compound comprising the structure of Formula II:

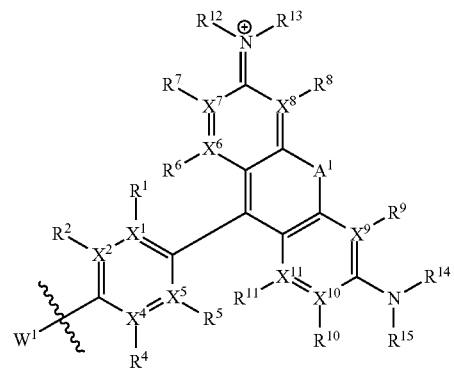

Formula II wherein, $A^1$ is selected from $SiH_2$, $SiHR'$, or $SiR'_2$, wherein R' is selected from the group consisting of D, optionally substituted FG, optionally substituted $(C_1-C_{12})$alkyl, optionally substituted $(C_1-C_{11})$heteroalkyl, optionally substituted $(C_1-C_{12})$alkenyl, optionally substituted $(C_1-C_{11})$heteroalkenyl, optionally substituted $(C_1-C_{12})$alkynyl, and optionally substituted $(C_1-C_{11})$heteroalkynyl;

$X^1$-$X^{11}$ are independently selected from N or C, wherein when an X group is an N, then the R group is absent; and $R^1$-$R^{15}$ are independently selected from H, D, optionally substituted FG, optionally substituted ($C_1$-$C_{12}$) alkyl, optionally substituted ($C_1$-$C_{11}$)heteroalkyl, optionally substituted ($C_1$-$C_{12}$)alkenyl, optionally substituted ($C_1$-$C_{11}$)heteroalkenyl, optionally substituted ($C_1$-$C_{12}$)alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system, $W^1$ is a molecular wire moiety; and wherein one of $R^1$ or $R^5$ is a sulfonate group.

2. The compound of claim 1, wherein the compound comprises the structure of Formula II(a):

Formula II(a)

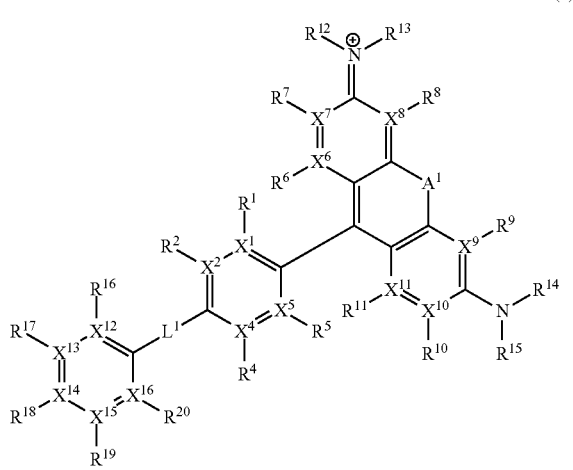

wherein, $L^1$ is selected from the group consisting of:

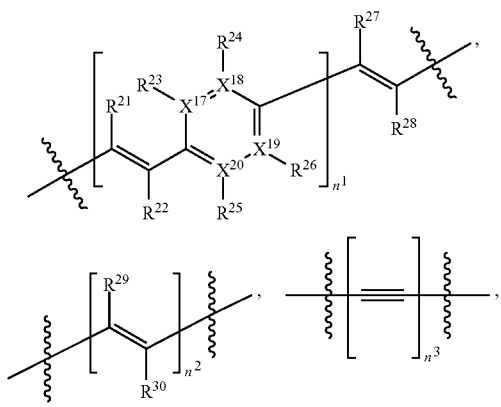

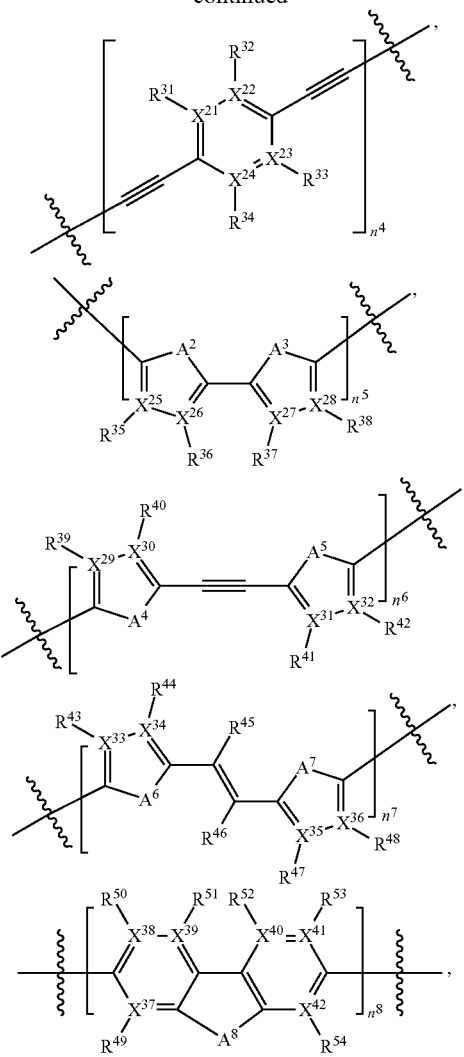

and any combination of the foregoing;
wherein
$A^1$ is selected from $SiH_2$, $SiHR'$, or $SiR'_2$;
$A^2$-$A^8$ are each independently selected from $CH_2$, $CHR'$, $CR'_2$, NH, O, S, Se, Te, $SiH_2$, $SiHR'$, $SiR'_2$, $GeH_2$, $GeHR'$, $GeR'_2$, $SnH_2$, $SnHR'$, $SnR'_2$, $PbH_2$, $PbHR'$, or $PbHR'_2$, wherein R' is selected from the group consisting of D, optionally substituted FG, optionally substituted ($C_1$-$C_{12}$)alkyl, optionally substituted ($C_1$-$C_{11}$) heteroalkyl, optionally substituted ($C_1$-$C_{12}$)alkenyl, optionally substituted ($C_1$-$C_{11}$)heteroalkenyl, optionally substituted ($C_1$-$C_{12}$)alkynyl, and optionally substituted ($C_1$-$C_{11}$)heteroalkynyl;
$X^1$, $X^2$, and $X^4$-$X^{42}$ are independently selected from N or C, wherein when an X group is an N, then the R group is absent;
$R^1$, $R^2$, and $R^4$-$R^{54}$ are independently selected from H, D, optionally substituted FG, optionally substituted ($C_1$-$C_{12}$)alkyl, optionally substituted ($C_1$-$C_{11}$)heteroalkyl, optionally substituted ($C_1$-$C_{12}$)alkenyl, optionally substituted ($C_1$-$C_{11}$)heteroalkenyl, optionally substituted ($C_1$-$C_{12}$)alkynyl, optionally substituted ($C_1$-$C_{11}$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system;

wherein one of $R^1$ or $R^5$ is a sulfonate group; and $n^1$-$n^8$ are independently an integer selected from 0 to 10.

3. The compound of claim 2, wherein the compound comprises the structure of Formula II(b):

substituted $(C_1$-$C_6)$alkyl, optionally substituted $(C_1$-$C_5)$heteroalkyl, optionally substituted $(C_1$-$C_6)$alkenyl, optionally substituted $(C_1$-$C_5)$heteroalkenyl, optionally substituted $(C_1$-$C_6)$alkynyl, optionally substituted $(C_1$-$C_5)$heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings

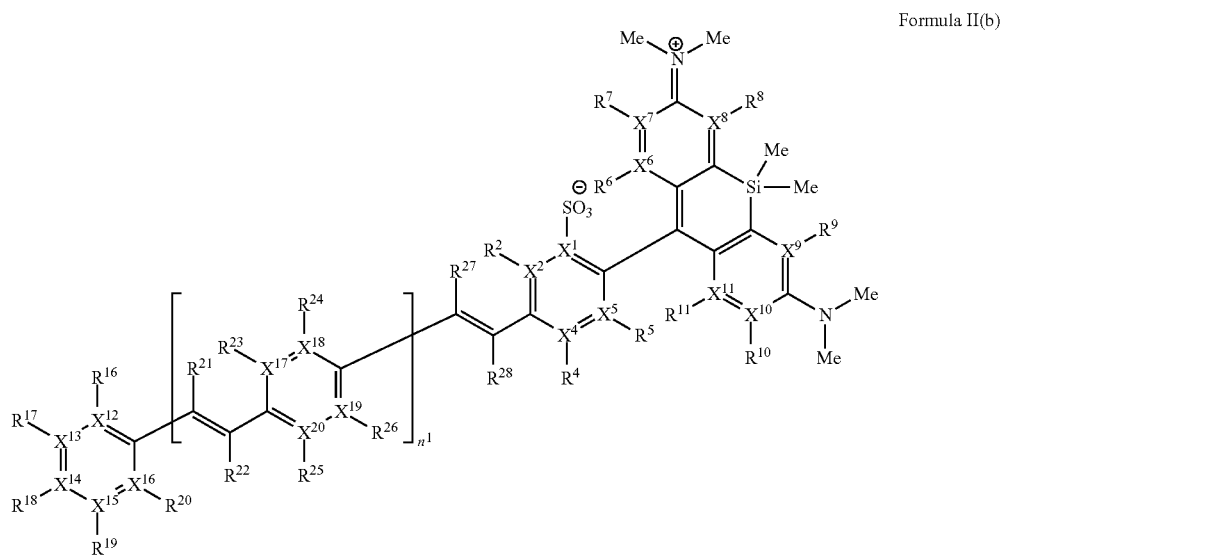

Formula II(b)

wherein, $X^1$, $X^2$, and $X^4$-$X^{20}$ are independently selected from N or C, wherein when an X group is an N, then the R group is absent;

$R^2$, $R^4$-$R^{11}$, and $R^{16}$-$R^{26}$ are independently selected from H, D, optionally substituted FG, optionally selected from the group comprising cycloalkyl, cycloalkenyl, heterocycle, aryl, and mixed ring system; and $n^1$ is an integer from 0 to 5.

4. The compound of claim 3, wherein the compound comprises the structure of Formula II(c):

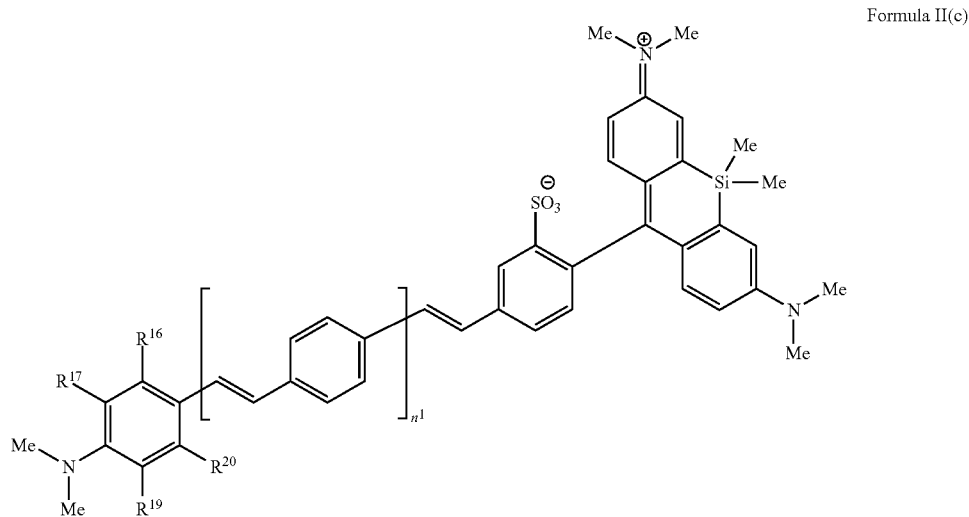

Formula II(c)

wherein, $R^{16}$, $R^{17}$, $R^{19}$ and $R^{20}$ are independently selected from H, D, optionally substituted FG, optionally substituted ($C_1$-$C_6$)alkyl, optionally substituted ($C_1$-$C_5$)heteroalkyl, optionally substituted ($C_1$-$C_6$)alkenyl, optionally substituted ($C_1$-$C_5$)heteroalkenyl, optionally substituted ($C_1$-$C_6$)alkynyl, optionally substituted ($C_1$-$C_5$)heteroalkynyl, optionally substituted cycloalkyl, optionally substituted cycloalkenyl, optionally substituted aryl, optionally substituted heterocycle, optionally substituted mixed ring system, wherein one or more adjacent R groups can be linked together to form one or more substituted rings selected from the group comprising cycloalkyl, cycloalkenyl, heterocycle, aryl, and mixed ring system;

$n^1$ is an integer from 0 to 5.

5. The compound of claim 4, wherein the compound comprises the structure of:

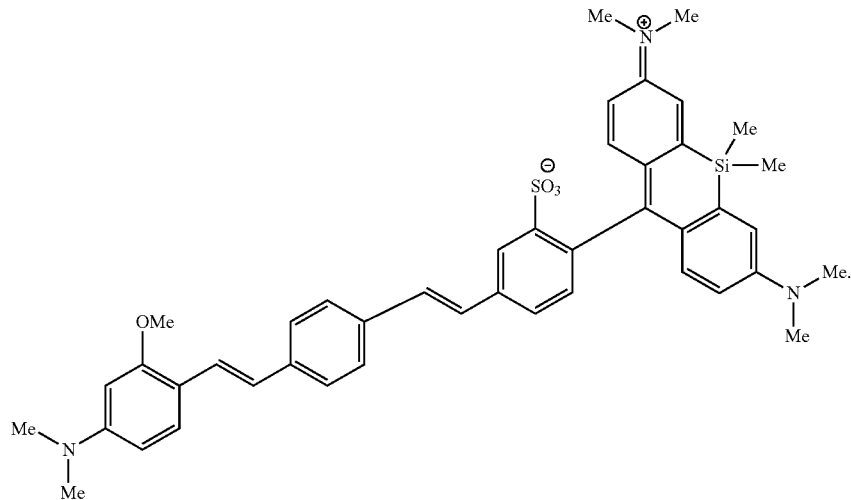

6. The compound of claim 1, wherein the compound has one or more of the following characteristics:

the compound emits far red to near infrared light upon excitation with incident light;

the compound is water soluble;

the compound exhibits minimal solvatochromism;

the compound does not undergo spirocyclization in either acidic or basic environments; and/or the compound can undergo photoinduced electron transfer.

7. The compound of claim 6, wherein the compound is characterized by emitting far red to near infrared light upon excitation with incident light; is water soluble; exhibits minimal solvatochromism; does not undergo spirocyclization in either acidic or basic environments; and can undergo photoinduced electron transfer.

* * * * *